(12) United States Patent
Yan et al.

(10) Patent No.: US 10,851,071 B2
(45) Date of Patent: Dec. 1, 2020

(54) M-DIHYDROXYBENZENE DERIVATIVE CRYSTAL AND SALT, AND MANUFACTURING METHOD THEREOF

(71) Applicant: Chia Tai Tianqing Pharmaceutical Group Co., Ltd., Lianyungang (CN)

(72) Inventors: Xiaobing Yan, Shanghai (CN); Wei Huang, Shanghai (CN); Dan Li, Shanghai (CN); Charles Z. Ding, Shanghai (CN); Fei Liu, Lianyungang (CN); Xiquan Zhang, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 127 days.

(21) Appl. No.: 16/318,606

(22) PCT Filed: Jul. 20, 2017

(86) PCT No.: PCT/CN2017/093674
§ 371 (c)(1),
(2) Date: Jan. 17, 2019

(87) PCT Pub. No.: WO2018/014858
PCT Pub. Date: Jan. 25, 2018

(65) Prior Publication Data
US 2019/0284146 A1 Sep. 19, 2019

(30) Foreign Application Priority Data
Jul. 21, 2016 (CN) .......................... 2016 1 0581808

(51) Int. Cl.
| | |
|---|---|
| *C07D 261/18* | (2006.01) |
| *C07D 261/08* | (2006.01) |
| *C07D 413/04* | (2006.01) |
| *A61P 35/00* | (2006.01) |
| *A61K 31/422* | (2006.01) |

(52) U.S. Cl.
CPC .......... *C07D 261/18* (2013.01); *A61K 31/422* (2013.01); *A61P 35/00* (2018.01); *C07D 261/08* (2013.01); *C07D 413/04* (2013.01); *C07B 2200/13* (2013.01)

(58) Field of Classification Search
CPC .. C07D 261/18; C07D 261/08; C07D 413/04; A61P 35/00; A61K 31/422; C07B 2200/13
See application file for complete search history.

(56) References Cited

U.S. PATENT DOCUMENTS

| | | | |
|---|---|---|---|
| 8,450,310 B2 | 5/2013 | Drysdale | |
| 10,035,792 B2 * | 7/2018 | Chen | ..................... C07D 487/04 |

FOREIGN PATENT DOCUMENTS

| | | |
|---|---|---|
| CA | 2974756 A1 | 7/2016 |
| CN | 1771235 A | 5/2006 |
| CN | 103724269 A | 4/2014 |
| WO | WO 2007/021966 A1 | 2/2007 |
| WO | WO 2016/116061 A1 | 7/2016 |

OTHER PUBLICATIONS

Jing, R. et al., "Progress in the study of small molecule inhibitors of HSP90," Acta Pharmaceutica Sinica 2015, 50 (6): 640-649 (10 pages).
International Search Report in International Application No. PCT/CN2017/093674, dated Oct. 18, 2017 (8 pages, w/English translation).
Written Opinion in International Application No. PCT/CN2017/093674, dated Oct. 18, 2017 (20 pages, w/English translation).

* cited by examiner

*Primary Examiner* — Timothy R Rozof
(74) *Attorney, Agent, or Firm* — Nixon Peabody LLP

(57) ABSTRACT

Provided are a crystal and salt of an m-dihydroxybenzene derivative represented by formula (I), a manufacturing method thereof, and an application of the crystal in preparing a pharmaceutical product for treating a HSP90-mediated disease.

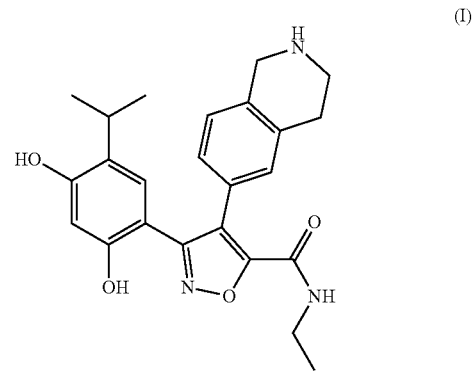

18 Claims, 6 Drawing Sheets

M-DIHYDROXYBENZENE DERIVATIVE CRYSTAL AND SALT, AND MANUFACTURING METHOD THEREOF

REFERENCE TO RELATED APPLICATIONS

The present application is a U.S. national stage of PCT/CN2017/093674 filed on Jul. 20, 2017, which claims the benefit of Chinese Patent Application No, 201610581808.2 filed on Jul. 21, 2016 in the State Intellectual Property Office of the P. R. China, which are incorporated by reference in their entireties.

FIELD OF THE INVENTION

The present invention relates to a crystal and salt of an m-dihydroxybenzene derivative, as well as a manufacturing method thereof.

BACKGROUND OF THE INVENTION

Currently, targeted therapies for cancer are based on the identification of specific proteins that promote tumor development, and the identification of specific agents that are capable of exerting the effect of antagonizing these proteins. Pharmaceutical industry mostly concentrates efforts on a very limited number of well-validated protein targets. A common drawback lies in that the frequent occurrence of drug-resistant mutations is found in cancer patients treated with these specific inhibitors. Recently, it is generally considered that simultaneous blocking of signaling pathways involved in cancer development is expected to be able to facilitate better anti-tumor effects, and also reduce the likelihood of drug-resistance development. HSP90 belongs to a small family of proteins (GHKL, derived from DNA gyrase, HSP90, histidine kinase, mutL) that generally share a very specific C-type pattern (Bergerat fold) linked to adenosine triphosphate. HSP90 is one of the most abundant proteins in cells and is essential for the viability of eukaryotes. Human cells contain four HSP90 isoforms: constitutively expressed cytosolic β-isoform, inducible α-form, GRP94/gp96 in endoplasmic reticulum, and TRAP1/HSP75 in mitochondria. The α- and β-forms show 85% sequence homology.

HSP90 is a key component of a chaperone structure, and catalyzes the folding of a so called client protein of HSP90 and the quality control in normal cells and under stress conditions. The activity of a molecular chaperone, which strictly depends on the activity of adenosine triphosphatase, is closely modulated by the binding of other regulatory co-chaperone molecules. There is strong evidence demonstrating that, in the case of disease states, for example, cancers or other proliferative diseases, HSP90 becomes critical due to mutations or overexpression of particular oncogenes, or due to tumors often having overloaded, misfolded proteins (which leads to an increased demand for the molecular chaperone function).

HSP90 is a homodimer composed of three kinds of main domains in structure: a very conserved N-terminal domain, an intermediate domain of adenosine triphosphatase domain and a C-terminal domain. The N- and C-terminal domains can bind to adenosine triphosphate. Most currently known inhibitors, such as geldanamycin, radicicol, diarylpyrazole and purine derivatives, exhibit competitive binding to the adenosine triphosphate at the N-terminal adenosine-binding site, while novobiocin is the prototype of an inhibitor that binds to the C-terminal pocket.

The client proteins of HSP90 currently reported are increasing (Jolly et at., J. Natl. Cancer Inst. 92; 1564-1572 (2000)), and the client proteins of HSP90 belong to kinase family (Her2, B-RAF V600E, bcr-Abl, Flt3, NPM-ALK, Akt, Npm-Alk, ZAP-70), transcription factor (p53, HIF), telomerase, and other molecular chaperones, most of which are closely related to the development of cancer. The ability of HSP90 for inhibiting damaged fold or stabilizing client proteins thereof results in proteasebased degradation of these unfolded proteins. The degradation of these client proteins is often used as a marker for HSP90 inhibition, and cells that overexpress Her2 are typically used, such as BT474 breast cancer cells, in which Her2 are degraded after treatment with compounds.

It has been demonstrated that, the natural compound geldanamycin can indeed block the proliferation of a variety of tumor cells through its abilities of competitively binding to the N-terminal adenosine triphosphate binding site and inhibiting the activity of HSP90 adenosine triphosphatase, which initially caused a lot of researches in the field of HSP90 inhibitors. Surprisingly, this compound is inactive in normal cells, which may be because that HSP90 is present in an active complex (with high affinity to geldanamycin) only existed in tumor cells (Kamal et al., Nature 425, 407-410 (2003)). Another possible reason for their selective sensitivity to tumors is the tumor retention exhibited by many HSP90 inhibitors.

A large number of clinical evaluations on semisynthetic derivatives of geldanamycin (GDA), tanespimycin (17AAG), and other related derivatives (alvespimycin, 17DMAG, IPI-504) are ongoing, but the effects thereof appear to be limited by a number of factors: complex preparations, production of active metabolites depending on metabolism, lack of enrichment of patients, and hepatotoxicity that may be associated with quinone moiety. This results in a great deal of effort to identify second-generation HSP90 inhibitors with better drug-like characteristics and better tolerance. This leads to the identification of purine derivatives and substituted aryl-resorcinol derivatives.

The main cause of neurodegenerative diseases such as Alzheimer's disease, Parkinson's disease, Huntington's disease and Prion disease is that the accumulation of misfolded proteins leads to the formation of plaque. These misfolded proteins undergo rematuration, depolymerization, and re-solubilization of protein aggregates depending on molecule chaperones (HSP70, HSP40, etc.). Heat shock proteins have been shown to provide this function in a variety of cell culture models. HSF1 can induce HSP, and HSF1 is closely regulated by HSP90 in normal cells. It has been proved that HSP90 inhibitors, such as geldanamycin and 17-AAG derivatives, can disrupt this interaction and lead to HSP induction, and then lead to neuroprotective activity as well as re-solubilization and depolymerization of misfolded proteins. Overexpression of HSP90 can significantly reduce the accumulation of misfolded proteins which is the cause of Alzheimer's disease. In fact, it has been proven that there is an anti-correlation between the levels of HSP70/90 and aggregated tau. Overexpression of HSP70, HSP27 and HSP40 can reduce abnormal tau aggregation (by degradation), which is triggered by an inhibition of HSP90. Based on the in vivo effect of GDA on neurotoxicity induced by 1methyl-4phenyl-1,2,3,6tetrahydropyridine (MPTP) in a mouse model of Parkinson's disease, HSP90 inhibitors are used for treating Parkinson's disease. GDA protects neurons from MPTP-induced toxicity, which is closely related to elevated levels of HSP70. In addition, it has also been shown that overexpression of HSP90 can significantly reduce the accumulation of misfolded proteins, which is the cause of sports injury, multiple sclerosis, spinal and bulbar muscular atrophy, and other diseases.

4,6-Disubstituted resorcinol compound with pharmacological activity is disclosed in GB 1,406,345. Phenyl-heterocyclic compounds, all of which are characterized by a specific substitution pattern with a five-membered heterocycle, are described as HSP90 inhibitors in other patent applications, for example, WO2006/101052 with the applicant of Nippon Kayaku Kabushiki Kaisha; WO2005/000300, WO2004/072051 and WO2004/056782 with the applicant of Vernalis; WO2003/055860 with the applicant of Ribotargets; WO2008/097640 with the applicant of Synta Pharmaceuticals, and WO2005/063222 with the applicant of Kyowa Hakko Kogyo.

WO2004072051 relates to a class of HSP90 inhibitors, including Luminespib:

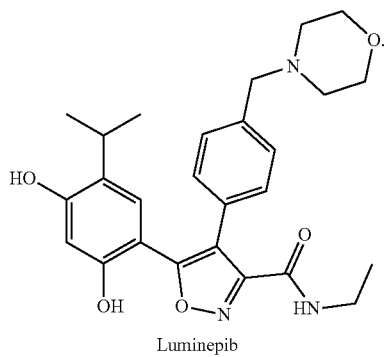 [SMILES: CCNC(=O)c1noc(-c2cc(C(C)C)c(O)cc2O)c1-c1ccc(CN2CCOCC2)cc1]

Luminepib

WO2006055760A1 reports some compounds, such as,

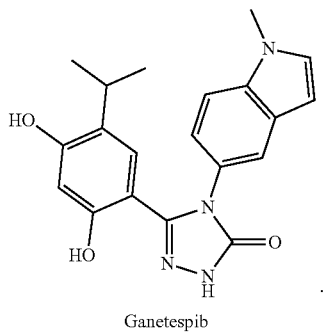 [SMILES: CC(C)c1cc(-c2n[nH]c(=O)n2-c2ccc3c(ccn3C)c2)c(O)cc1O]

Ganetespib

CN1771235A discloses some compounds, such as,

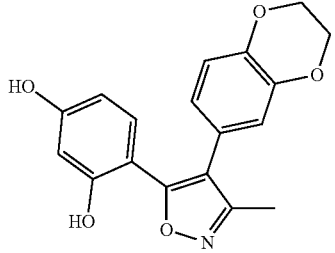

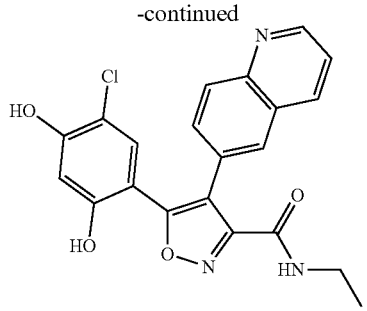

These compounds are not desirable in terms of efficacy, pharmacokinetics, water solubility, druggability and the like. Despite the above developments, there is still a need to develop HSP90 inhibitors that are more effective and lower side effects.

SUMMARY OF THE INVENTION

The present invention provides a compound of formula (I) in crystalline form,

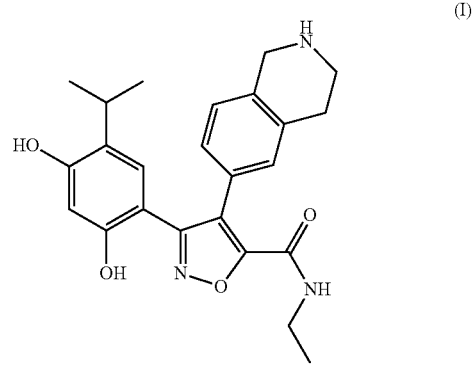 [SMILES: CCNC(=O)c1onc(-c2cc(C(C)C)c(O)cc2O)c1-c1ccc2c(c1)CCNC2]

(I)

In one embodiment, the present invention provides a compound of formula (I) in crystalline form, and the crystalline form is A-type crystal.

In some embodiments of the present invention, a X-ray powder diffraction pattern for the A-type crystal of the compound of formula (I) has diffraction peaks at the following 2θ angles: 10.66±0.2°, 15.09±0.2°, 19.17±0.2°.

In some embodiments of the present invention, the X-ray powder diffraction pattern for the A-type crystal of the compound of formula (I) has diffraction peaks at the following 2θ angles: 10.66±0.2°, 11.41±0.2°, 15.09±0.2°, 19.17±0.2°, 20.43±0.2°, 22.19±0.2°, 25.76±0.2°.

In some embodiments of the present invention, the X-ray powder diffraction pattern for the A-type crystal of the compound of formula (I) has diffraction peaks at the following 2θ angles: 10.66±0.2°, 11.41±0.2°, 15.09±0.2°, 17.85±0.2°, 19.17±0.2°, 19.60±0.2°, 20.43±0.2°, 21.81±0.2°, 22.19±0.2°, 25.76±0.2°.

In some embodiments of the present invention, the X-ray powder diffraction pattern for the A-type crystal of the compound of formula (I) has diffraction peaks at the following 2θ angles: 10.66±0.2°, 11.41±0.2°, 15.09±0.2°, 15.84±0.2°, 17.85±0.2°, 18.22±0.2°, 19.17±0.2°, 19.60±0.2°, 20.19±0.2°, 20.43±0.2°, 21.81±0.2°, 22.19±0.2°, 22.86±0.2°, 24.57±0.2°, 25.76±0.2°, 26.05±0.2°, 27.75±0.2°.

In some embodiments of the present invention, analysis data of the X-ray powder diffraction pattern for the above A-type crystal of the compound of formula (I) are shown in Table 1.

In some embodiments of the present invention, the X-ray powder diffraction pattern for the above A-type crystal of the compound of formula (I) is shown in FIG. 1.

In some embodiments of the present invention, a differential scanning calorimetry curve for the above A-type crystal of the compound of formula (I) has a starting point of endothermic peaks at 198±5° C.

In some embodiments of the present invention, the differential scanning calorimetry curve for the above A-type crystal of the compound of formula (I) is shown in FIG. 2.

In some embodiments of the present invention, the method for preparing the above A-type crystal of the compound of formula (I) comprises the following steps:

(1) adding the compound of formula (I) into a solvent, stirring at 70-100° C. until completely dissolved;

(2) naturally cooling to 0-30° C. under stirring, and continuing to stir and crystallize under such temperature condition;

(3) filtering, collecting the solids and drying the same.

Wherein, the solvent is water, methanol, ethanol, isopropanol, tert-butanol, acetone, 2butanone, benzene, toluene, xylene, diethyl ether, tert-butyl methyl ether, tetrahydrofuran, 2methyltetrahydrofuran or 1,4dioxane.

In some embodiments of the present invention, the method for preparing the above A-type crystal of the compound of formula (I) comprises the following steps:

(1) adding the compound of formula (I) into a solvent, stirring at 15-40° C. for 1-48 hours and then centrifuging;

(2) filtering, collecting the solids and drying the same.

Wherein, the solvent is a single solvent selected from acetone, methanol, ethanol, isopropanol, tetrahydrofuran or 1,4dioxane; or a mixed solvent of water and any one of solvents each independently selected from methanol, ethanol, acetonitrile and isopropanol; in one embodiment of the present invention, the volume ratio of any one of methanol, ethanol, acetonitrile and isopropanol to water is 3:1.

The present invention also provides a crystalline composition of the above A-type crystal. Wherein, the crystalline composition of the A-type crystal means that with respect to the total weight of the composition, the weight of the A-type crystal of the compound of formula (I) in the composition is 50% or more, preferably 70% or more, more preferably 90% or more, and most preferably 95% or more, while a small amount of other crystals or amorphous substances of the compound of formula (I) may be included in the composition, including but not limited to, B-type crystal, C-type crystal, D-type crystal or amorphous substances of the compound of formula (I).

In one embodiment, the present invention provides a compound of formula (I) in crystalline form, and said crystal is a B-type crystal.

In some embodiments of the present invention, a X-ray powder diffraction pattern for the B-type crystal of the compound of formula (I) has diffraction peaks at the following 2θ angles: 7.34±0.2°, 14.69±0.2°, 22.15±0.2°.

In some embodiments of the present invention, the X-ray powder diffraction pattern for the B-type crystal of the compound of formula (I) has diffraction peaks at the following 2θ angles: 7.34±0.2°, 12.23±0.2°, 12.53±0.2°, 14.69±0.2°, 18.72±0.2°, 19.03±0.2°, 20.67±0.2°, 22.15±0.2°.

In some embodiments of the present invention, analysis data of the X-ray powder diffraction pattern for the above B-type crystal of the compound of the formula (I) is shown in Table 2.

In some embodiments of the present invention, the X-ray powder diffraction pattern for the above B-type crystal of the compound of formula (I) is shown in FIG. 3.

In some embodiments of the present invention, a differential scanning calorimetry curve for the above B-type crystal of the compound of Formula (I) has a starting point of endothermic peaks at 55±5° C.

In some embodiments of the present invention, the differential scanning calorimetry curve for the above B-type crystal of the compound of formula (I) is shown in FIG. 4.

The present invention also provides a crystalline composition of the above B-type crystal. Wherein, the crystalline composition of the B-type crystal means that with respect to the total weight of the composition, the weight of the B-type crystal of the compound of formula (I) in the composition is 50% or more, preferably 70% or more, more preferably 90% or more, and most preferably 95% or more, while a small amount of other crystals or amorphous substances of the compound of formula (I) may be included in the composition, including but not limited to, A-type crystal, C-type crystal, D-type crystal or amorphous substances of the compound of formula (I).

In one embodiment, the present invention provides a compound of formula (I) in crystalline form, and said crystal is a C-type crystal.

In some embodiments of the present invention, a X-ray powder diffraction pattern for the C-type crystal of the compound of formula (I) has diffraction peaks at the following 2θ angles: 6.45±0.2°, 7.68±0.2°, 12.91±0.2°, 13.58±0.2°.

In some embodiments of the present invention, the X-ray powder diffraction pattern for the C-type crystal of the compound of formula (I) has diffraction peaks at the following 2θ angles: 6.45±0.2°, 7.68±0.2°, 10.56±0.2°, 12.91±0.2°, 13.58±0.2°, 15.40±0.2°, 21.14±0.2°, 26.32±0.2°.

In some embodiments of the present invention, the X-ray powder diffraction pattern for the C-type crystal of the compound of formula (I) has diffraction peaks at the following 2θ angles: 6.45±0.2°, 7.68±0.2°, 10.56±0.2°, 12.91±0.2°, 13.58±0.2°, 15.40±0.2°, 16.72±0.2°, 21.14±0.2°, 23.16±0.2°, 25.74±0.2°, 26.32±0.2°.

In some embodiments of the present invention, analysis data of the X-ray powder diffraction pattern for the above C-type crystal of the compound of formula (I) is shown in Table 3.

In some embodiments of the present invention, the X-ray powder diffraction pattern for the above C-type crystal of the compound of formula (I) is shown in FIG. 5.

In some embodiments of the present invention, a differential scanning calorimetry curve for the above C-type crystal of the compound of Formula (I) has a starting point of endothermic peaks at 108±5° C.

In some embodiments of the present invention, the differential scanning calorimetry curve for the above C-type crystal of the compound of Formula (I) is shown in FIG. 6.

The present invention also provides a crystalline composition of the above C-type crystal. Wherein, the crystalline composition of the C-type crystal means that with respect to the total weight of the composition, the weight of the C-type crystal of the compound of formula (I) in the composition is 50% or more, preferably 70% or more, more preferably 90% or more, and most preferably 95% or more, while a small amount of other crystals or amorphous substances of the compound of formula (I) may be included in the composition, including but not limited to, A-type crystal, B-type crystal, D-type crystal or amorphous substances of the compound of formula (I).

In one embodiment, the present invention provides a compound of formula (I) in crystalline form, and said crystal is a D-type crystal.

In some embodiments of the present invention, a X-ray powder diffraction pattern for the D-type crystal of the compound of formula (I) has diffraction peaks at the following 2θ angles: 5.96±0.2°, 9.53±0.2°, 19.43±0.2°.

In some embodiments of the present invention, the X-ray powder diffraction pattern for the D-type crystal of the compound of formula (I) has diffraction peaks at the following 2θ angles: 5.96±0.2°, 9.53±0.2°, 9.65±0.2°, 11.94±0.2°, 16.42±0.2°, 19.43±0.2°, 22.01±0.2°, 25.49±0.2°.

In some embodiments of the present invention, the X-ray powder diffraction pattern for the D-type crystal of the compound of formula (I) has diffraction peaks at the following 2θ angles: 5.96±0.2°, 9.53±0.2°, 9.65±0.2°, 11.94±0.2°, 12.46±0.2°, 14.43±0.2°, 14.92±0.2°, 16.42±0.2°, 19.43±0.2°, 20.26±0.2°, 22.01±0.2°, 23.06±0.2°, 25.49±0.2°, 27.15±0.2°.

In some embodiments of the present invention, analysis data of the X-ray powder diffraction pattern for the above D-type crystal of the compound of formula (I) is shown in Table 4.

In some embodiments of the present invention, the X-ray powder diffraction pattern for the above D-type crystal of the compound of formula (I) is shown in FIG. 7.

In some embodiments of the present invention, a differential scanning calorimetry curve for the above D-type crystal of the compound of formula (I) has a starting point of the endothermic peaks at 141±5° C.

In some embodiments of the present invention, the differential scanning calorimetry curve for the above D-type crystal of the compound of formula (I) is shown in FIG. 8.

The present invention also provides a crystalline composition of the above D-type crystal. Wherein, the crystalline composition of the D-type crystal means that with respect to the weight of the composition, a weight of the D-type crystal of the compound of formula (I) in the composition is 50% or more, preferably 70% or more, more preferably 90% or more, and most preferably 95% or more, while a small amount of other crystals or amorphous substances of the compound of formula (I) may be included in the composition, including but not limited to, A-type crystal, B-type crystal, C-type crystal or amorphous substances of the compound of formula (I).

Hereinafter, A-type crystal or the crystalline composition of A-type crystal, B-type crystal or the crystalline composition of B-type crystal, C-type crystal or the crystalline composition of C-type crystal, D-type crystal or the crystalline composition of D-type crystal of the compound of formula (I); trifluoroacetate, methanesulfonate, ρ-toluenesulfonate, citrate, maleate, fumarate, hydrobromide, phosphate and sulfate of the compound of formula (I); the compound of formula (II) such as the compound of formula (II-1) or formula (II-2) in the present invention are collectively refers to as "the active substance of the present invention".

The active substance of the present invention can be administrated by any administration routes suitable for the diseases to be treated, including the administration routes such as oral, topical (e.g., buccal, sublingual, etc.), parenteral (e.g., subcutaneous, intramuscular, intravenous, spinal, intradermal, intrathecal, etc.), rectal, vaginal.

Although the active substance of the present invention can be administrated in the form of a pure substance, it is usually administrated in the form of a pharmaceutical composition. The pharmaceutical composition of the active substance of the present invention further comprises one or more pharmaceutical excipients, and may further comprise other therapeutically active ingredients if needed. It can also be administrated in combination with the therapy of chemotherapy, radiation therapy, and surgery.

Dosage forms of the pharmaceutical compositions suitable for oral administration include tablet, capsule, powder, granule, dripping pill, paste, pulvis, tincture, syrup and the like, preferably tablet and capsule. Wherein, the tablet may be a common tablet, a dispersible tablet, an effervescent tablet, a sustained-release tablet, a controlled-release tablet or an enteric-coated tablet, and the capsule may be a common capsule, a sustained-release capsule, a controlled-release capsule or an enteric-coated capsule.

The amount of the active substance of the present invention in unit formulation of the tablets and capsules for oral administration may vary depending on the treatment status of patients and specific administration routes.

The present invention provides a salt of the above compound of formula (I), which may be selected from trifluoroacetate, methanesulfonate, ρ-toluenesulfonate, citrate, maleate, fumarate, hydrobromide, phosphate and sulfate. The skilled in the art can understand that in the above salts, the compound of formula (I) and acids may be present in any proportion which is chemically reasonable.

The present invention also provides a salt of the compound of formula (I) represented by the following formula (II),

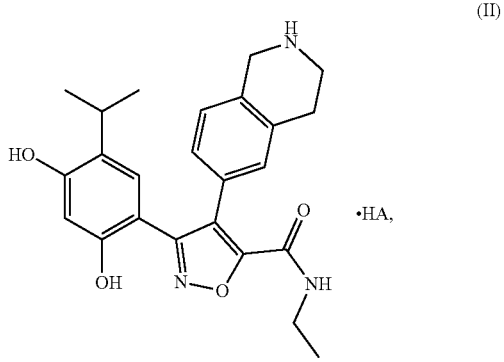

wherein, HA is selected from trifluoroacetic acid, methanesulfonic acid, ρ-toluenesulfonic acid, citric acid, maleic acid, fumaric acid, hydrochloric acid, hydrobromic acid, phosphoric acid and sulfuric acid.

The skilled in the art can understand that in the above compound of formula (II), the compound of the formula (I) and the acid may be present in any proportion which is chemically reasonable, for example, the ratio of the compound of the formula (I) to the acid is 1:1 or 1:0.5.

The present invention also provides a method for preparing the above salt of the compound of formula (I) (that is, a compound of formula (II)),

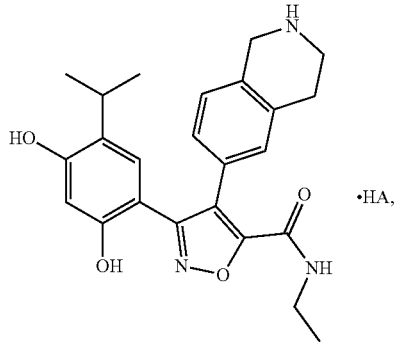

comprising the following steps:

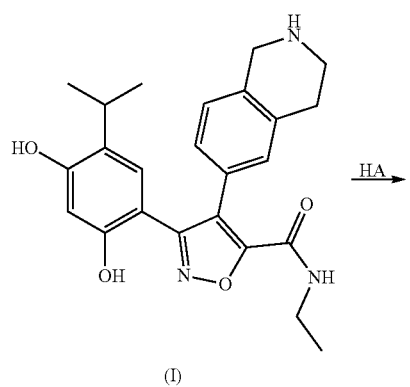

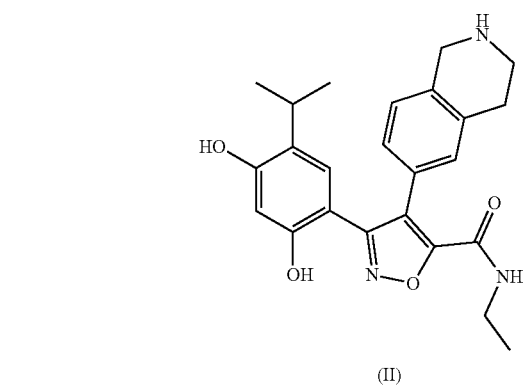

wherein, HA is selected from trifluoroacetic acid, methanesulfonic acid, ρ-toluenesulfonic acid, citric acid, maleic acid, fumaric acid, hydrochloric acid, hydrobromic acid, phosphoric acid and sulfuric acid.

The present invention also provides a compound represented by formula (II-1):

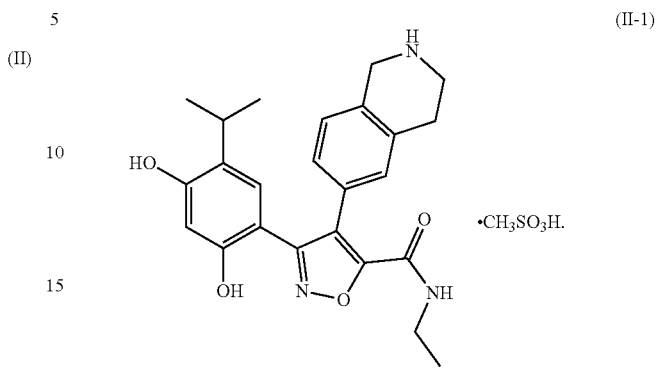

The present invention also provides a compound represented by formula (II-2):

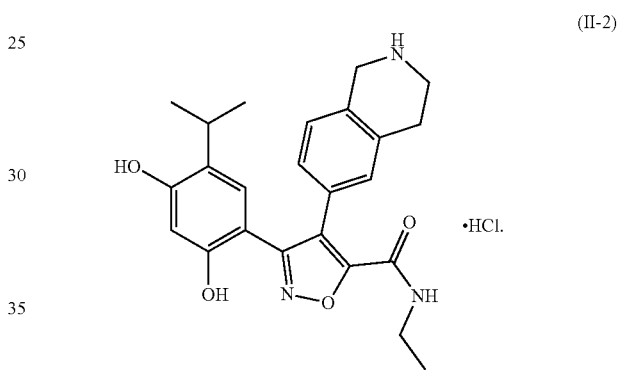

The present invention also provides a pharmaceutical composition comprising the above compound of formula (I) in the crystalline form, and the crystalline composition.

The present invention also provides a pharmaceutical composition comprising the following: trifluoroacetate, methanesulfonate, ρ-toluenesulfonate, citrate, maleate, fumarate, hydrobromide, phosphate or sulfate of the compound of formula (I), or the compound of formula (II) such as the compound of formula (II-1) or the compound of formula (II-2).

The present invention also provides the above compound of formula (I) in crystalline form, or the crystalline composition, or the salt of the compound of formula (I), or the pharmaceutical composition thereof for use in the treatment of a HSP90-mediated disease; wherein the salt of the compound of formula (I) can be selected from trifluoroacetate, methanesulfonate, ρ-toluenesulfonate, citrate, maleate, fumarate, hydrobromide, phosphate or sulfate of the compound of formula (I), or the compound of the formula (II) such as the compound of formula (II-1) or the compound of formula (II-2).

The present invention also provides use of the above compound of formula (I) in crystalline form, or the crystalline composition, or the pharmaceutical composition thereof in the preparation of a medicament for the treatment of a HSP90-mediated disease.

The present invention also provides use of the trifluoroacetate, methanesulfonate, ρ-toluenesulfonate, citrate, maleate, fumarate, hydrobromide, phosphate or sulfate of the compound of formula (I), or the compound of formula (II) such as the compound of formula (II-1) or the compound of formula (II-2), or the pharmaceutical composition thereof in the preparation of a medicament for the treatment of a HSP90-mediated disease.

The present invention also provides a method for treating a HSP90-mediated disease, wherein the method comprises administering the above compound of formula (I) in crystalline form, or the crystalline composition, or the pharmaceutical composition to a subject in need thereof.

The present invention also provides a method for treating a HSP90-mediated disease, wherein the method comprises administering the above trifluoroacetate, methanesulfonate, ρ-toluenesulfonate, citrate, maleate, fumarate, hydrobromide, phosphate or sulfate of the compound of formula (I), or the compound of formula (II) such as the compound of formula (II-1) or the compound of formula (II-2), or the pharmaceutical composition thereof to a subject in need thereof.

The HSP90-mediated disease according to the present invention is selected from cancer and neurodegenerative disorder. Wherein, the cancer includes, but is not limited to, bladder cancer, breast cancer, colon cancer, kidney cancer, liver cancer, lung cancer including small cell lung cancer, esophageal cancer, gallbladder cancer, ovarian cancer, pancreatic cancer, gastric cancer, cervical cancer, thyroid cancer, prostate cancer, and skin cancer including squamous cell carcinoma; lymphatic hematopoietic tumors, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, and Burkitt's lymphoma; myeloid hematopoietic carcinomas, including acute and chronic myelogenous leukemia, myelodysplastic syndrome and promyelocytic leukemia; mesenchyme-derived cancer including fibrosarcoma and rhabdomyosarcoma; cancers of central and peripheral nervous system, including astrocytoma, neurocytoma, glioma, and neurilemmoma; and other cancers, including melanoma, seminoma, teratocarcinoma, osteosarcoma, xeroderma pigmentosum, keratoxanthoma, thyroid follicular carcinoma, and Kaposi's sarcoma. Wherein, the neurodegenerative disorder includes, but is not limited to, Alzheimer's disease, Parkinson's disease, Huntington's disease, multiple sclerosis, and spinal and bulbar muscular atrophy.

Definitions and Introductions

Unless otherwise indicated, the following terms and phrases as used herein are intended to have the following meanings. A particular phrase or term should not be considered to be indefinite or unclear in the absence of a specific definition, but should be interpreted as its ordinary meanings. When a trade name appears herein, it is intended to refer to the corresponding commodity or active ingredient thereof.

The intermediate compounds of the present invention can be prepared by a variety of synthesis methods well known by the skilled in the art, including the following exemplified embodiments, embodiments formed by combining the above embodiments with other chemical synthesis methods, and equivalent alternatives well known to the skilled in the art, and preferred embodiments include, but are not limited to, the examples of the present invention.

The chemical reactions in the specific embodiments of the present invention are completed in appropriate solvents, which should be suitable for the chemical changes of the present invention as well as the required reagents and materials thereof. In order to obtain the compounds of the present invention, sometimes the skilled in the art needs to make modifications or alternatives to synthetic steps or reaction processes on the basis of existing embodiments.

One important consideration factor in any synthetic route planning in this field is selecting suitable protecting groups for reactive functional groups (such as an amino group in the present invention). For the skilled artisan, "Greene and Wuts, Protective Groups In Organic Synthesis, Wiley and Sons, 1991" is authoritative in this regard. All references cited in the present invention are incorporated into the present invention in their entirety.

The present invention will be specifically described by examples below, which do not mean any limitations to the present invention.

All solvents used in the present invention are commercially available and can be used without further purification. Reactions are generally carried out under inert nitrogen in an anhydrous solvent. Proton nuclear magnetic resonance data are recorded on Bruker Avance III 400 (400 MHz) spectrometer, and chemical shift is expressed in ppm at downfield from tetramethylsilane. Mass spectra are measured on Agilent 1200 Series Plus 6110 (&1956A). LC/MS or Shimadzu MS contains one DAD detector: SPD-M20A (LC) and Shimadzu Micromass 2020 detector. The mass spectrometer is equipped with an electrospray ion source (ESI) operated in positive or negative mode.

The present invention employs the following abbreviations: DCM represents dichloromethane; PE represents petroleum ether; EA represents ethyl acetate; DMF represents N,N-dimethylformamide; EtOAc represents ethyl acetate; tol represents toluene; THF represents tetrahydrofuran; EtOH represents ethanol; MeOH represents methanol; OTf represents trifluoroacetoxy; MTBE represents methyl tert-butyl ether; Bn represents benzyl; Boc represents tert-butyloxycarbonyl, an amine protecting group; $Boc_2O$ represents di-tert-butyl dicarbonate; HCl (g) represents hydrogen chloride gas; $H_2SO_4$ represents sulfuric acid; HOAc represents acetic acid; TFA represents trifluoroacetic acid; TsOH represents ρ-toluenesulfonic acid; mCPBA represents m-chloroperoxybenzoic acid; CAN represents ammonium ceric nitrate; $BCl_3$ represents boron trichloride; $BBr_3$ represents boron tribromide; $TiCl_4$ represents titanium tetrachloride; $SOCl_2$ represents thionyl chloride; $(COCl)_2$ represents oxalyl chloride; DIPEA represents diisopropylethylamine; DIEA represents diisopropylethylamine; NMM represents N-methylmorpholine; DBU represents 1,8-diazabicycloundec-7ene; $Et_3N$ represents triethylamine; TEA represents triethylamine; t-BuOK represents potassium t-butoxide; KOAc represents potassium acetate; OAc represents acetoxy; NaClO represents sodium hypochlorite; $NaClO_2$ represents sodium chlorite; $KMnO_4$ represents potassium permanganate; $MnO_2$ represents manganese dioxide; HATU represents O-(7-azabenzotriazol-1-yl)-N,N,N',N'-tetramethyluronium hexafluorophosphate; HOBt represents 1-hydroxybenzotriazole; EDCl represents 1-(3dimethylam inopropyl)-3-ethylcarbodiimide; BOP-Cl represents bis(2oxo-3oxazolidinyl)phosphinic chloride; CDl represents carbonyldiimidazole; $T_3P$ represents 2,4,6Tripropyl-1,3,5,2, 4,6-trioxatriphosphinane 2,4,6trioxide; $NH_4Cl$ represents ammonium chloride; $PPh_3$ represents triphenylphosphine; NCS represents N-chlorosuccinimide; NBS represents N-bromosuccinimide; NIS represents N-iodosuccinimide; ICl represents iodine chloride; $I_2$ represents iodine; TEMPO represents 2,2,6,6-tetramethylpiperidinooxy; Pd represents palladium; Pd/C represents palladium carbon; Pt represents platinum; Rh represents rhodium; $PtO_2$ represents platinum dioxide; Pd(OH)$_2$ represents palladium hydroxide; Pd$_2$(dba)$_3$ represents tris(dibenzylideneacetone) dipalladium; Pd(PPh$_3$)$_4$ represents tetrakistriphenylphosphine palladium; Pd(dppf)Cl$_2$ represents 1,1'-bis(diphenylphosphino)ferrocene dichloropalladium (II); Pd(PPh$_3$)$_2$Cl$_2$ represents bis(triphenylphosphine)palladium(II) dichloride; Pd(OAc)$_2$ represents palladium acetate; PdCl$_2$ represents palladium chloride; CuI represents cuprous iodide; CuBr represents cuprous bromide; CuCl represents cuprous chloride; Cu represents copper powder; Cu$_2$O represents cuprous oxide; NMO represents N-methylmorpholine N-oxide; Luminespib represents 5[2,4dihydroxy-5-isopropylphenyl]-N-ethyl-4[4-(4-morpholinylmethyl)phenyl]-3-isoxazolecarboxamide; Ganetespib represents 3(2,4dihydroxy-5-isopropylphenyl)-4-(1methylindol-5-yl)-5-hydroxy-4H-1,2,4triazole; Cremophor represents polyoxyethylene castor oil.

The compounds are named manually or by the ChemDraw® software, and the supplier's catalog names are used for the commercially available compounds.

The process for synthesizing the compound of formula (I) and the intermediate thereof provided by the present invention has the following beneficial effects: the starting materials are cheap and easy to obtain; and disadvantages, such as high toxic reagents being used, harsh reaction conditions, low yields of routes, difficulties in separation, purification and industrialization, are overcome.

Specifically:

1) The raw materials used in the method for preparing the compound of formula (I) in the present invention are conventional or common reagents, which are readily available on the market and cheap;

2) The water solubility of the compound of formula (I) in the present invention can be effectively improved by forming salts thereof when preparing it;

3) The A-, B-, C- and D-type crystals of the compound of formula (I) provided by the present invention have stable properties, good solubility and hygroscopicity, as well as good prospects for druggability. Wherein, under the conditions of RT/92.5% RH (placed for 5 days), RT/92.5% RH (placed for 10 days), 60° C. (placed for 5 days), 60° C. (placed for 10 days), being grinded (investigation time: 10 min/20 min/30 min), respectively, the A-type crystal of the compound of formula (I) has no crystal transformation. Further, the wet weight gain ΔW % of the A-type crystal of the compound of formula (I) at 25±1° C. and 80±2% RH is about 0.45%, as shown in FIG. 9.

The trifluoroacetate, methanesulfonate, p-toluenesulfonate, citrate, maleate, fumarate, hydrobromide, phosphate and sulfate of the above compound of formula (I) provided by the present invention have stable properties and good hygroscopicity. Wherein, under the condition of 25±1° C. and 80±2% RH, the wet weight gain ΔW % of the methylsulfonate of the compound of formula (I) is about 1.742%, as shown in FIG. 10; the wet weight gain ΔW % of the maleate of the compound of formula (I) is about 0.379%, as shown in FIG. 11; and the wet weight gain ΔW % of the sulfate of the compound of formula (I) is about 0.081%, as shown in FIG. 12.

Method for X-ray powder diffractometer (XRPD) of the present invention

Instrument model: Bruker D8 advance X-ray diffractometer

Test conditions: Detailed XRPD parameters are as follows:

X-ray generator: Cu, kα, (λ=1.54056 Å)
Tube voltage: 40 kV, tube current: 40 mA.
Divergence slit: 0.60 mm
Detector slit: 10.50 mm
Anti-scatter slit: 7.10 mm
Scaning range: 4-40 deg
Step diameter: 0.02 deg
Step length: 0.12 seconds
Rotation speed of sample tray: 15 rpm.

It should be noted that, in XRD, the diffraction spectrum obtained from a crystalline compound is often characteristic for a specific crystal, wherein relative intensities of the bands (especially at low angles) may vary depending on preferential orientation effects resulting from the differences in crystallization conditions, particle sizes and others measurement conditions. Therefore, relative intensities of diffraction peaks are not characteristic for the targeted crystal, and it is the relative positions of the peaks rather than the relative intensities thereof to which more attention should be paid when judging whether crystals are the same as the known crystals. In XRD pattern, the position of a peak is usually expressed in terms of 2θ angle or interplanar spacing d. Since 2θ angle is related to the wavelength of incident X-ray, expressing in terms of interplanar spacing d is more representative. There is a simple conversion relationship between the two parameters: d=λ/2 sin θ, wherein d represents the interplanar spacing, λ, represents the wavelength of the incident X-ray, and θ represents the diffraction angle. It should also be noted that, in the identification of a mixture, some of diffracted rays are missing due to factors such as a decrease in content. At this time, even several bands may be characteristic for a given crystal without depending on the whole bands observed in a high purity sample.

Method of differential Scanning calorimeter (DSC) of the present invention

Instrument model: TA Q2000 Differential Scanning calorimeter

Test method: samples (~1 mg) were taken and placed in a DSC aluminum pan for testing, and heated from 25° C. to 350° C. at a heating rate of 10° C./min under 50 mL/min of N$_2$.

DSC measures the transition temperature when a crystal absorbs or releases heat due to changes in crystal structure thereof or crystal melting. In a continuous analysis for the same kind of crystal of the same compound, the error of the thermal transition temperature and melting point is typically within about 5° C., typically within about 3° C. When referring to a compound with a given DSC peak or melting point, this means that the DSC peak or melting point is within±3° C. DSC provides an auxiliary method for distinguishing different crystals. Different crystalline forms can be identified based on their characteristically different transition temperatures. It should be noted that, the DSC peak or melting point of a mixture may vary over a wider range. In addition, because of the decomposition accompanied the melting process of substances, the melting temperature is closely related to the heating rate.

DETAILED DESCRIPTION OF THE INVENTION

Figure 1:
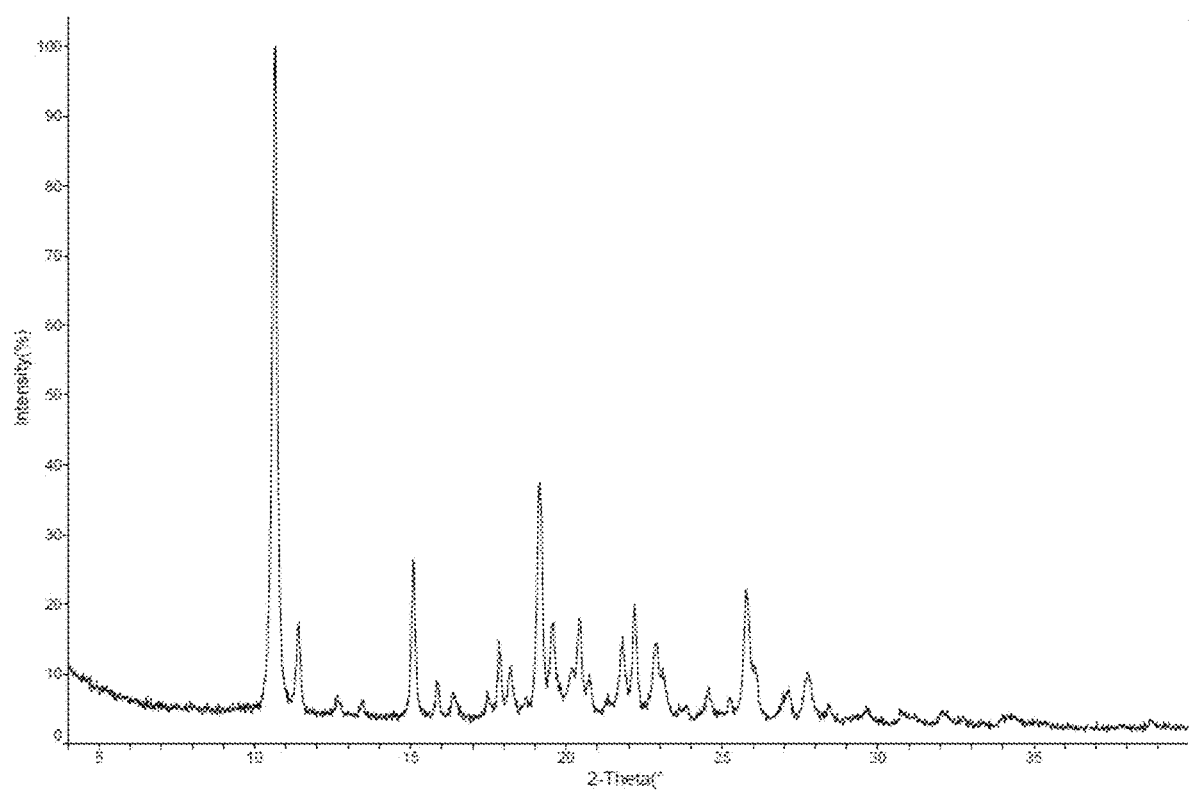
FIG. 1 is the XRPD spectrum of Cu-Kα radiation for A-type crystal of the compound of formula (I).
Figure 2:
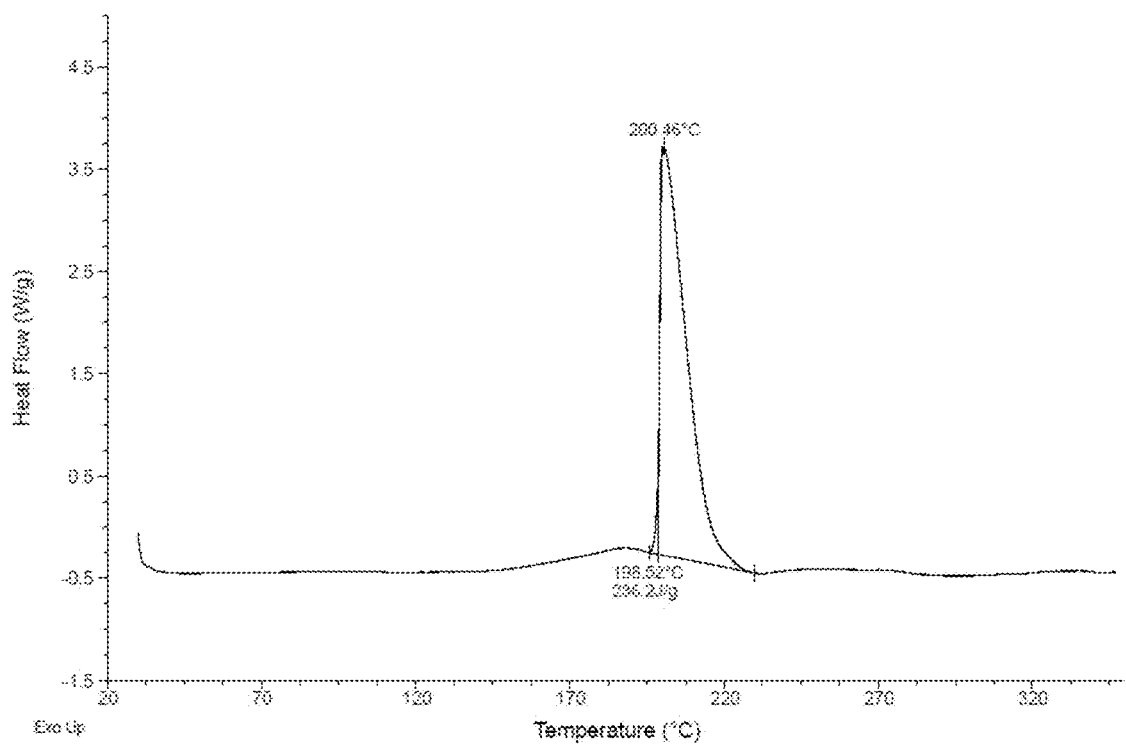
FIG. 2 is the DSC spectrum for A-type crystal of the compound of formula (I).
Figure 3:
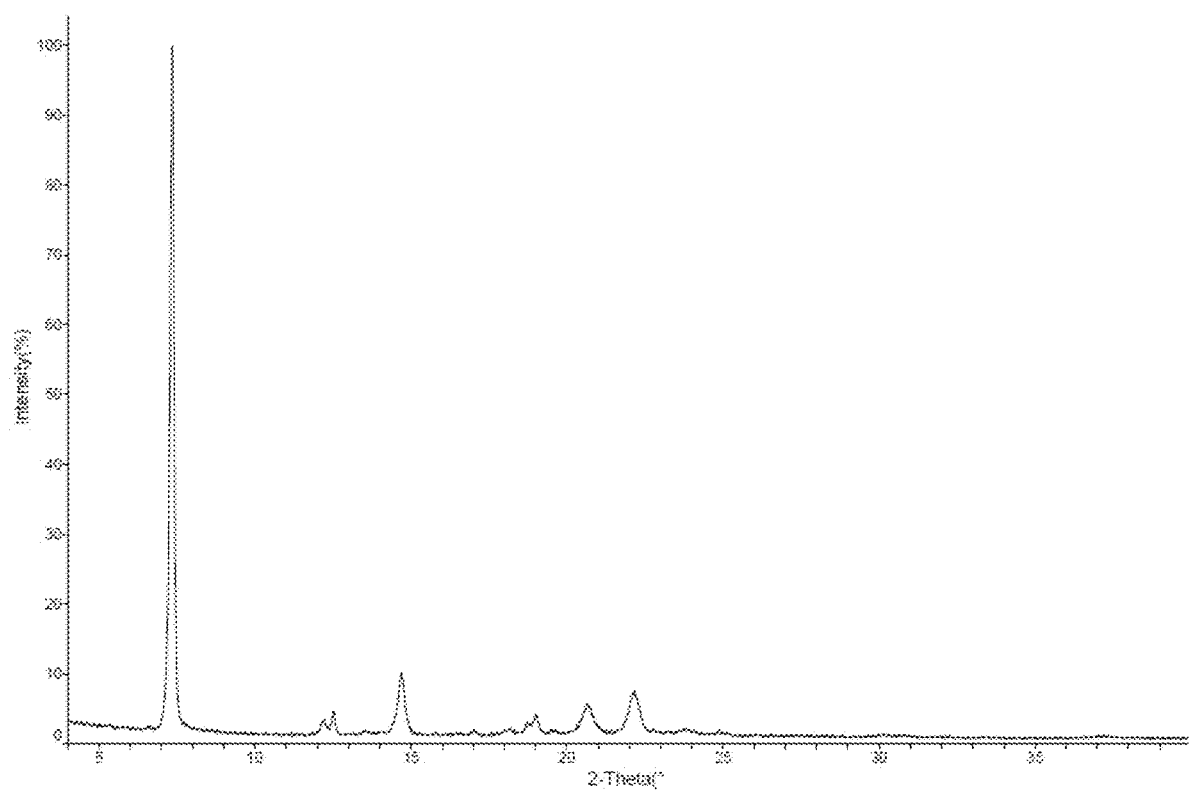
FIG. 3 is the XRPD spectrum of Cu-Kα radiation for B-type crystal of the compound of formula (I).
Figure 4:
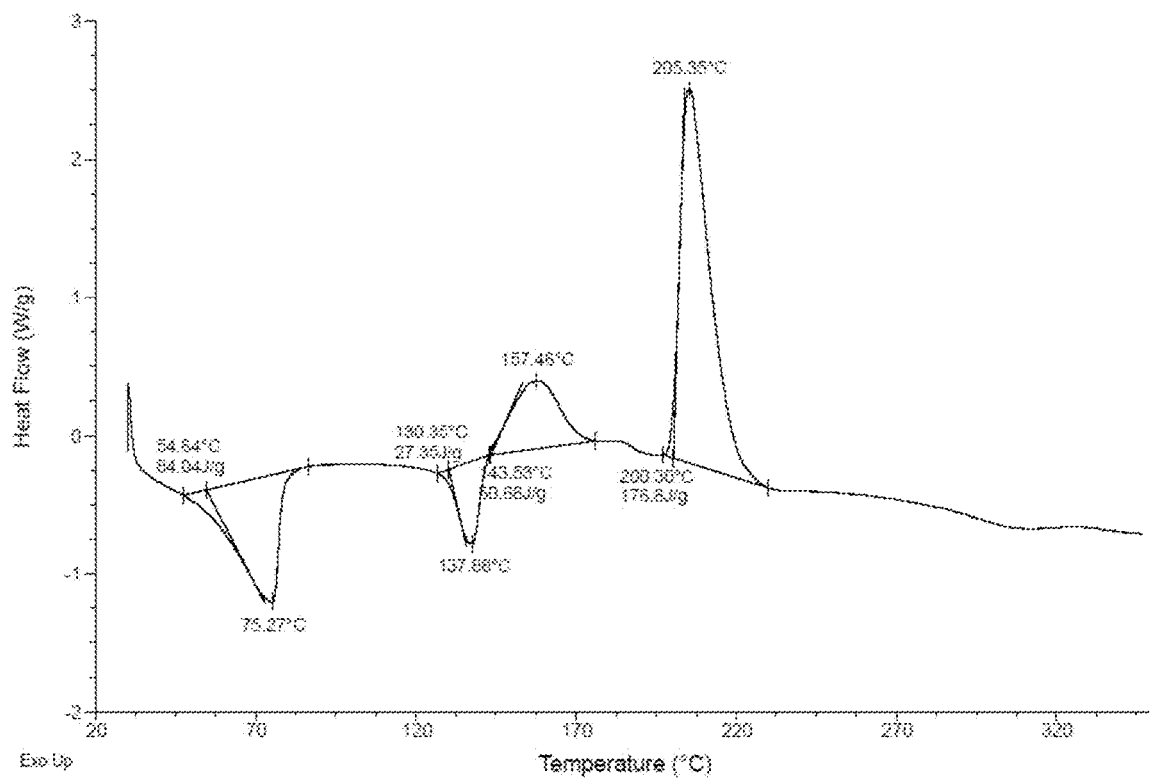
FIG. 4 is the DSC spectrum for B-type crystal of the compound of formula (I).
Figure 5:
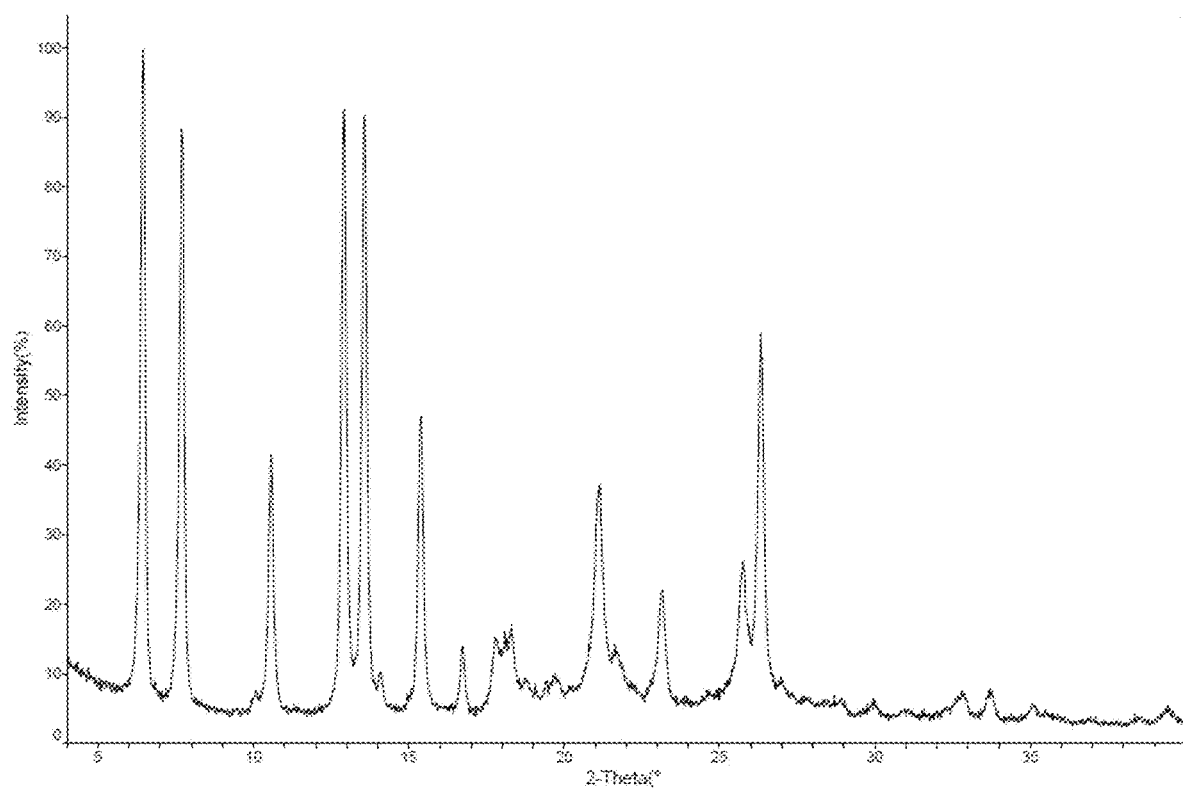
FIG. 5 is the XRPD spectrum of Cu-Kα radiation for C-type crystal of the compound of formula (I).
Figure 6:
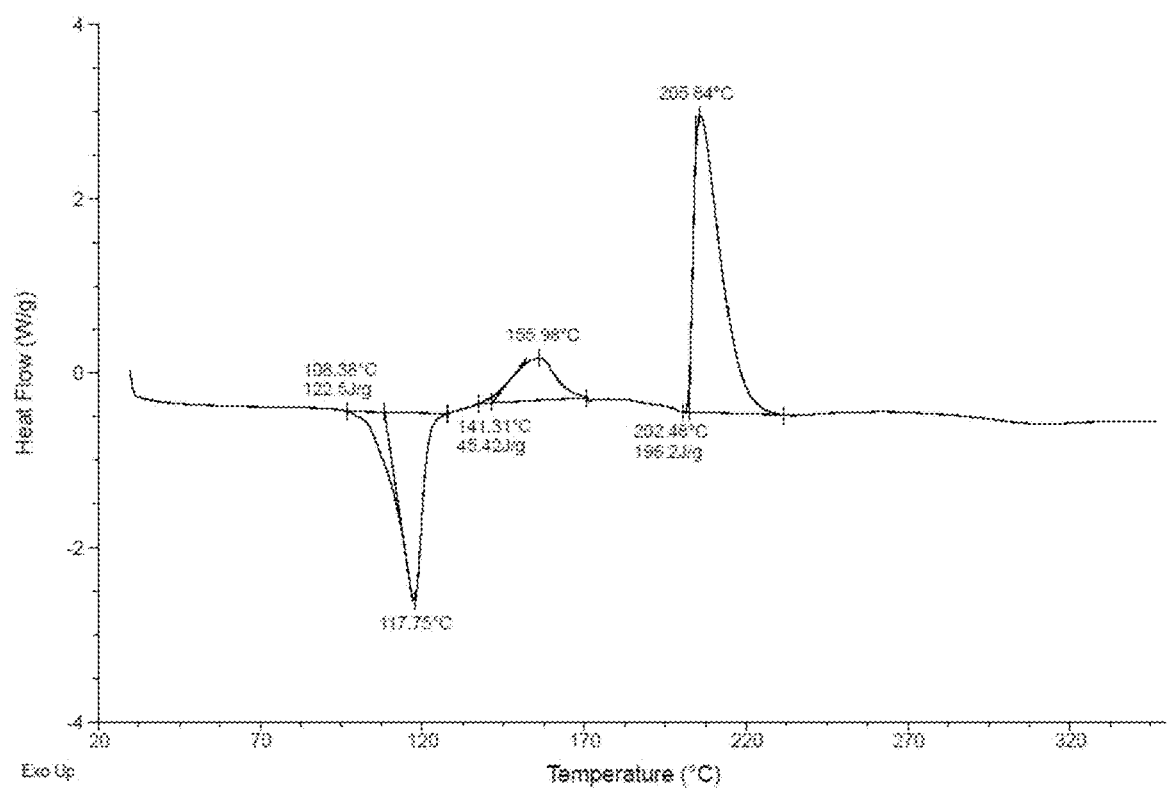
FIG. 6 is the DSC spectrum for C-type crystal of the compound of formula (I).
Figure 7:
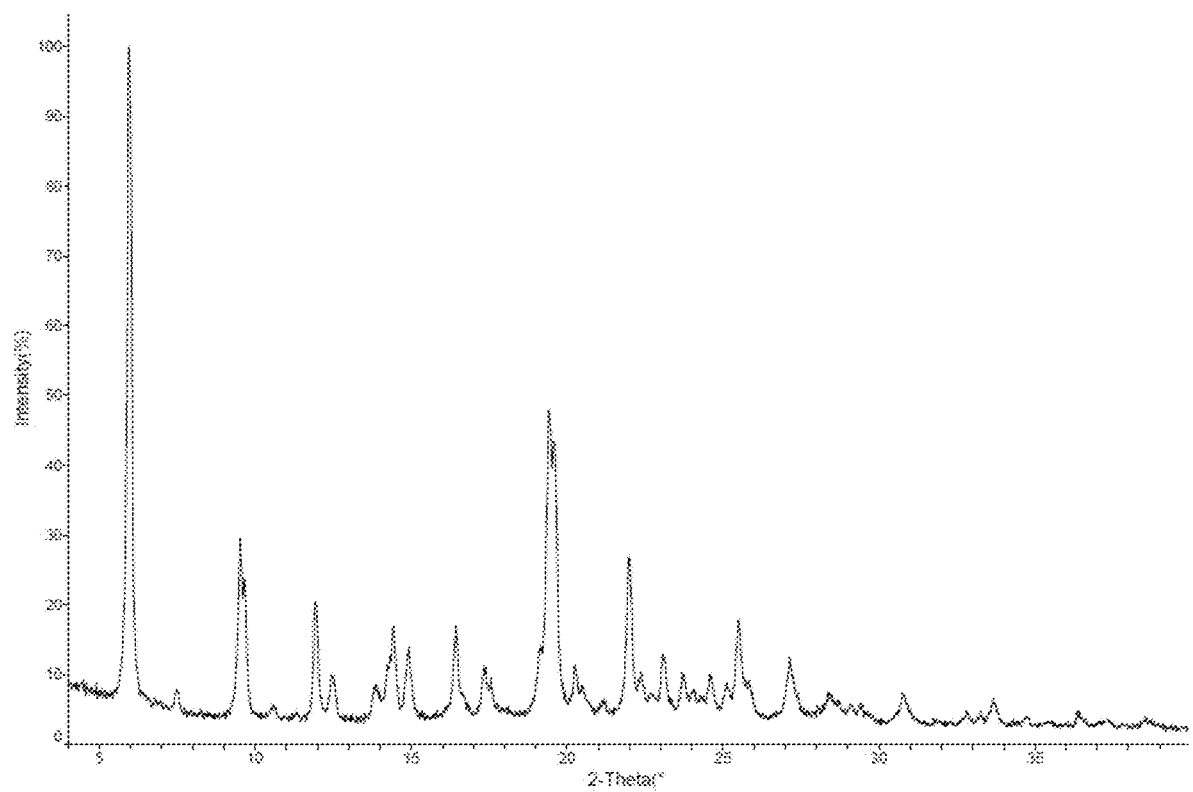
FIG. 7 is the XRPD spectrum of Cu-Kα radiation for D-type crystal of the compound of Formula (I).
Figure 8:
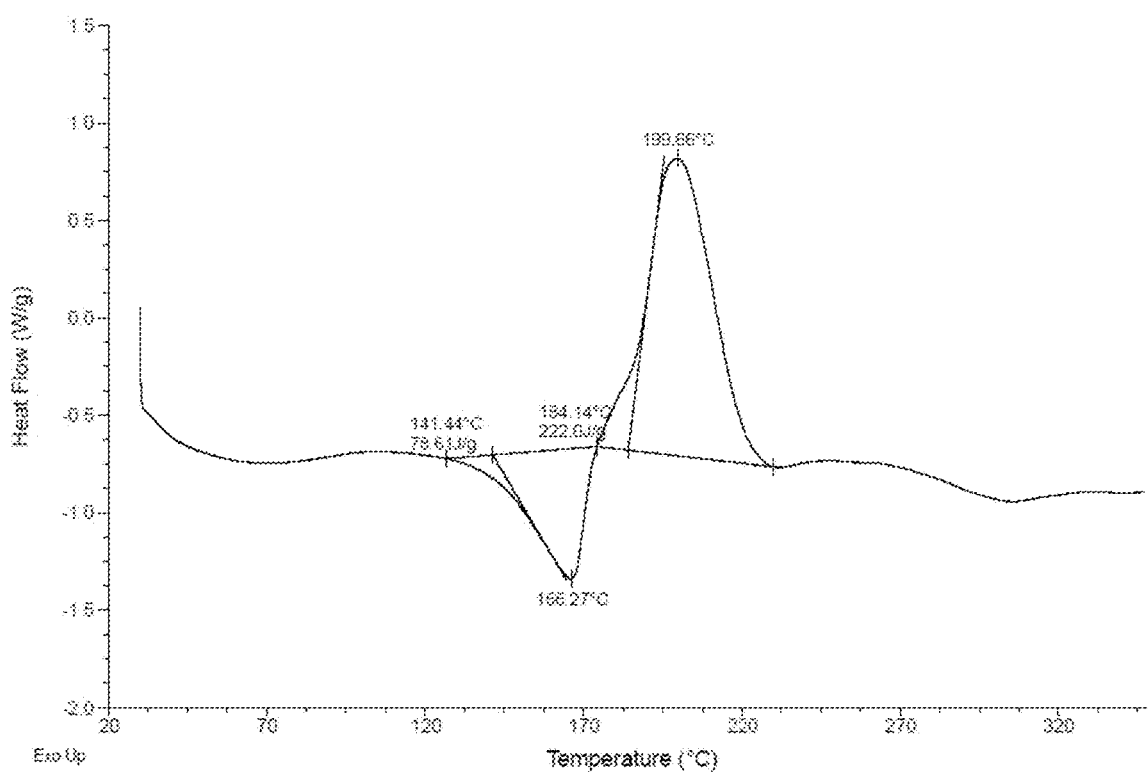
FIG. 8 is the DSC spectrum for D-type crystal of the compound of formula (I).
Figure 9:
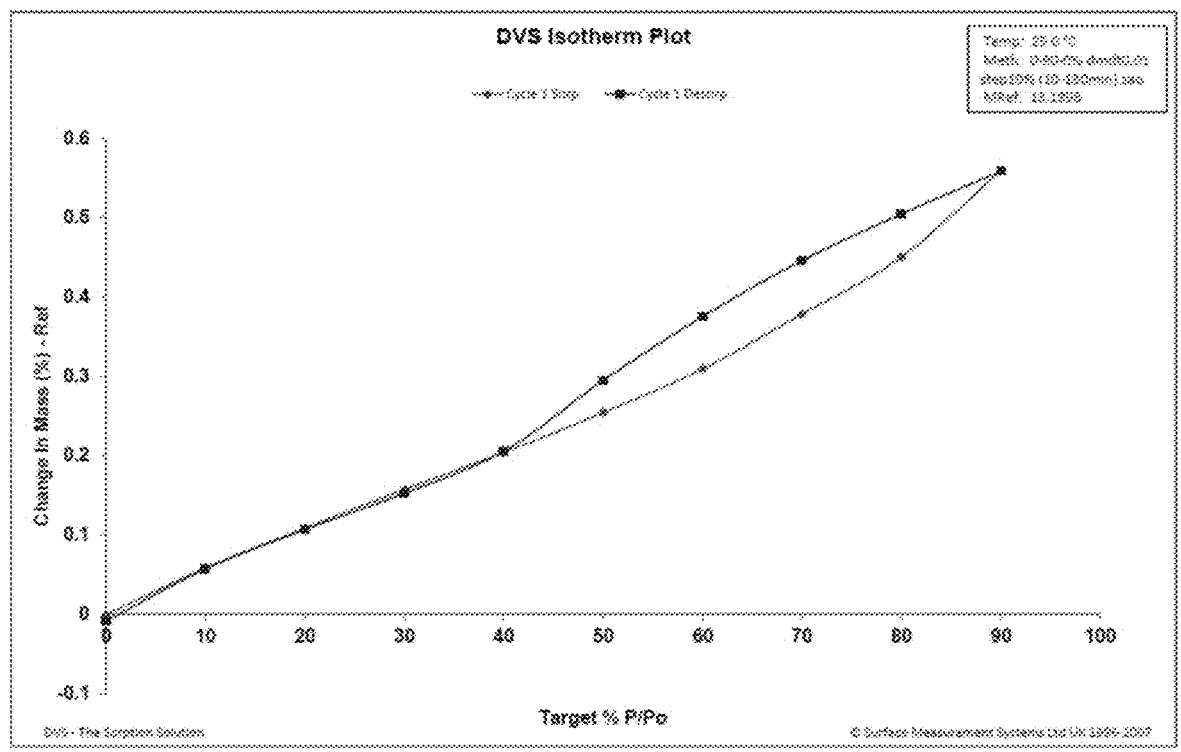
FIG. 9 is the dynamic vapour sorption (DVS) plot for A-type crystal of the compound of formula (I).
Figure 10:
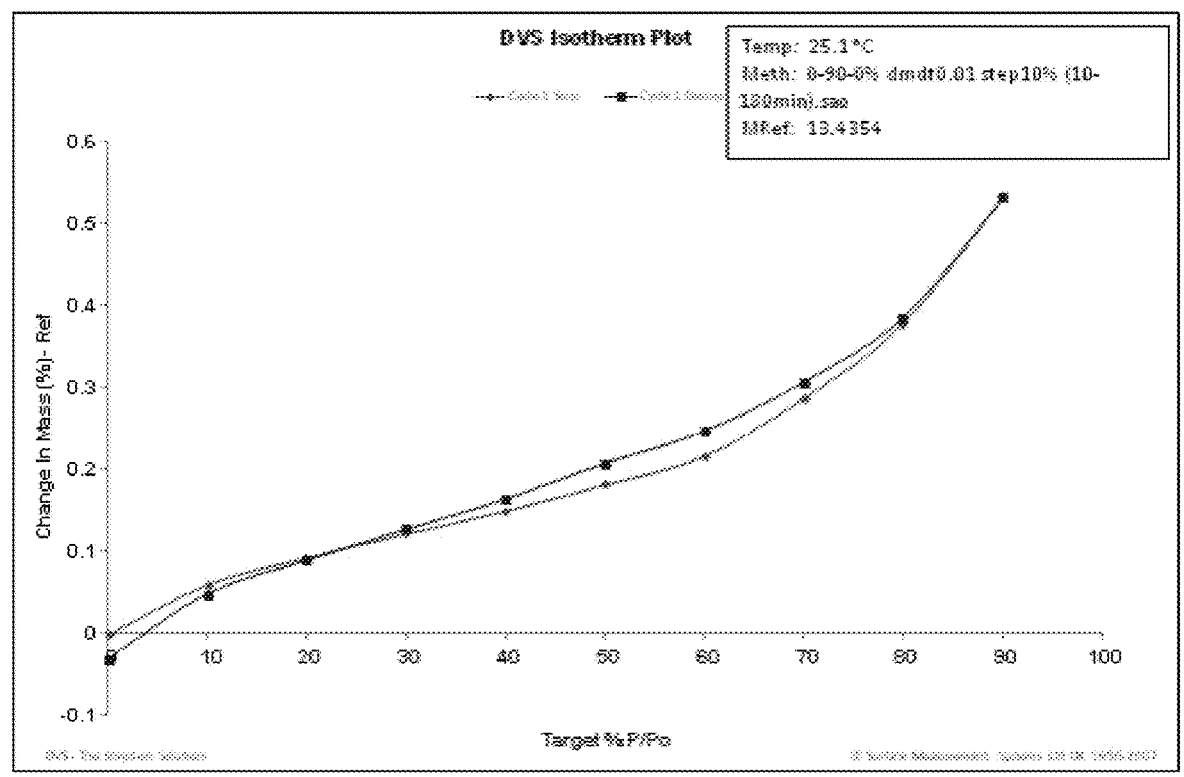
FIG. 10 is the dynamic vapour sorption (DVS) plot for the methanesulfonate of the compound of formula (I).
Figure 11:
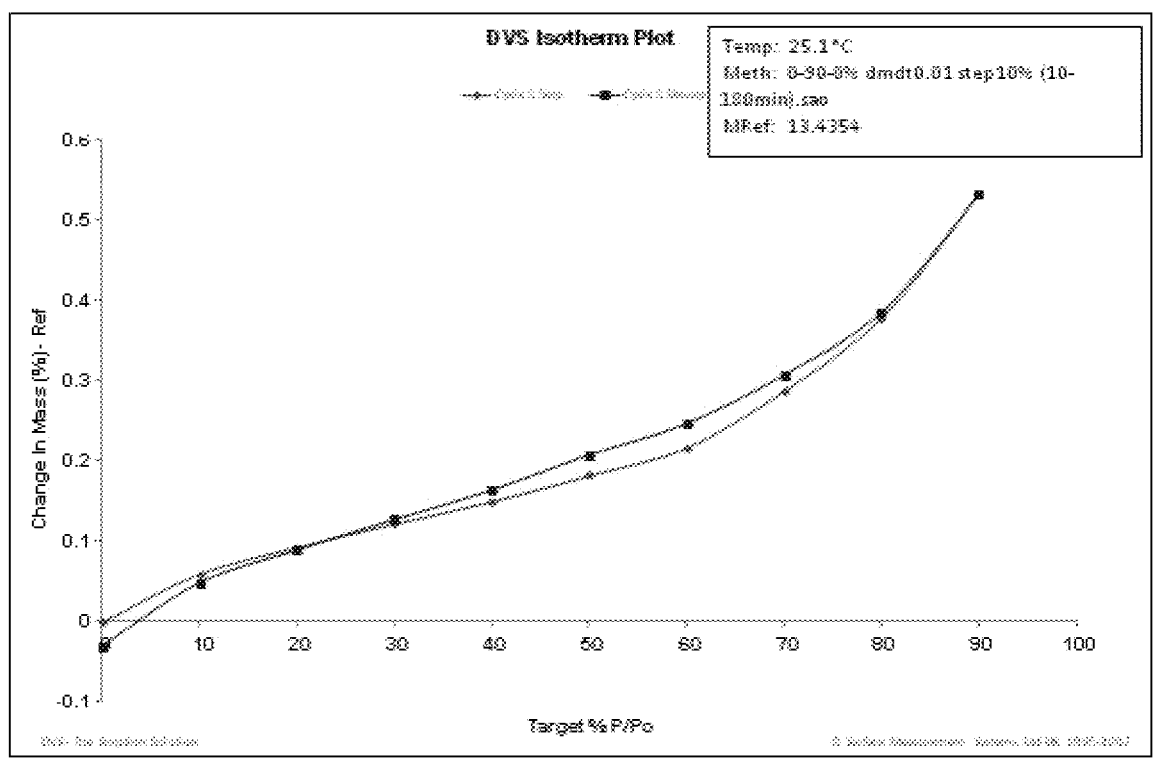
FIG. 11 is the dynamic vapour sorption (DVS) plot for the maleate of the compound of formula (I).
Figure 12:
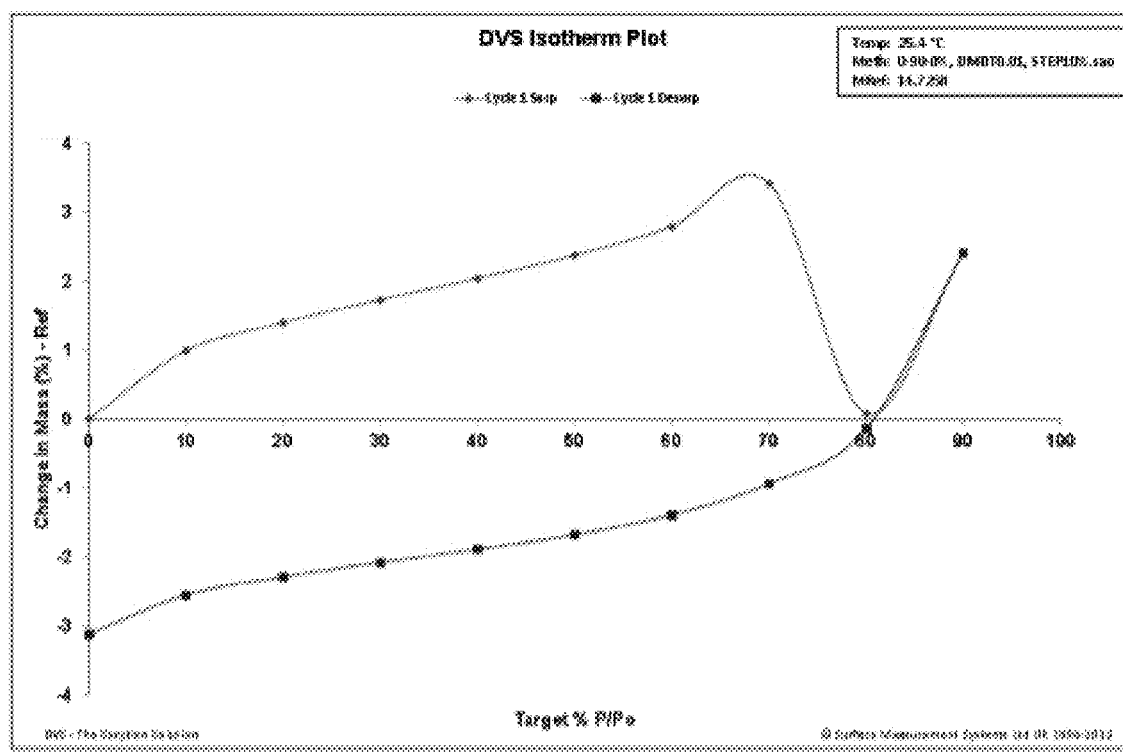
FIG. 12 is the dynamic vapour sorption (DVS) plot for the sulfate of the compound of formula (I).

Hereinafter, in order to better understand the content of the present invention, further illustrations are made in combination with the specific Examples. However, the specific Examples are not intended to limit the scope of the present invention.

EXAMPLE 1

Preparation of the Compound of Formula (I)

Preparation of Compound 10:

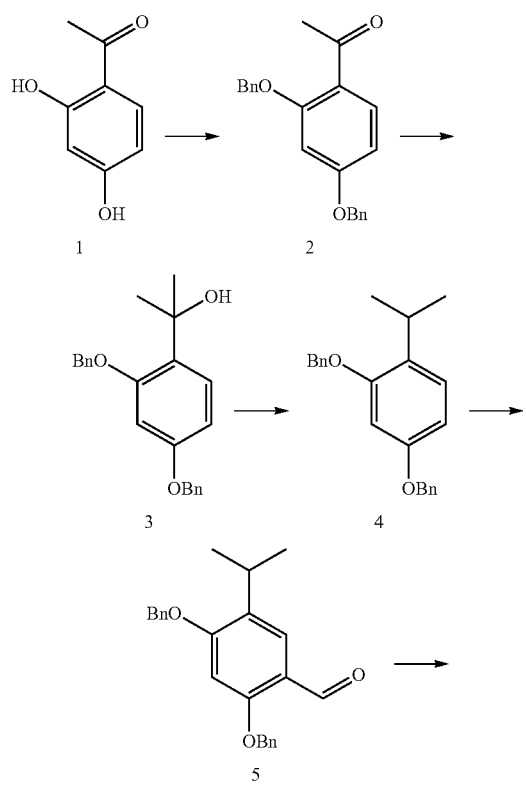

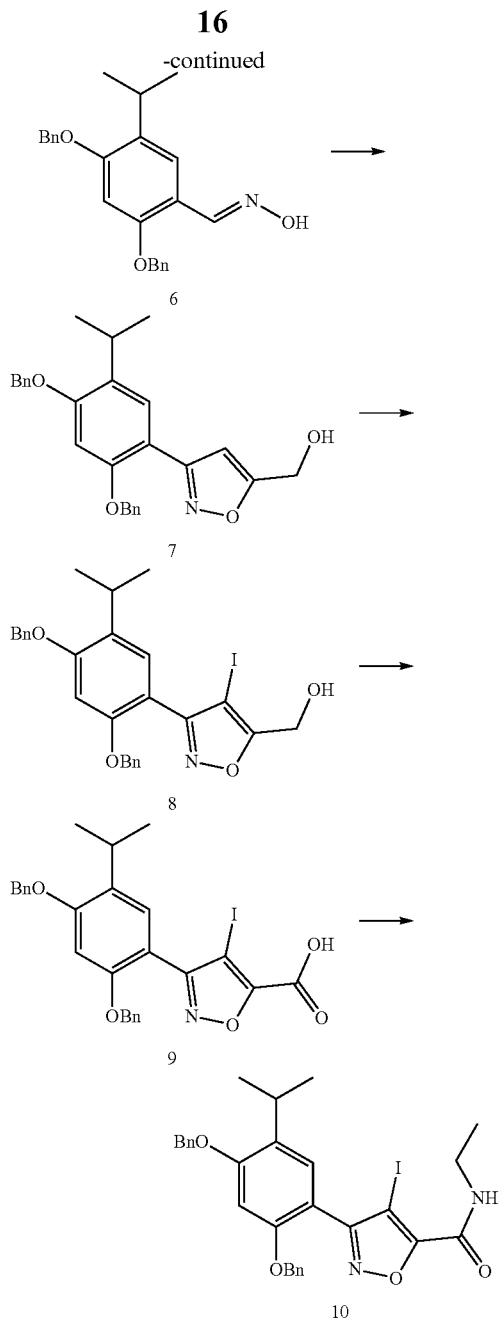

Step 1:

At room temperature, benzyl bromide (8.66 kg, 50.61 mol, 6.01 L, 2.20 equivalents), potassium iodide (190.93 g, 1.15 mol, 0.05 equivalents) and potassium carbonate (9.54 kg, 69.01 mol, 3.00 equivalents) were added to a solution of 1-(2,4dihydroxyphenyl)ethanone (3.50 kg, 23.00 mol, 2.97 L, 1.00 equivalent) in acetonitrile (24 L), and then heated to 85° C. and stirred for 16 hours. After the reaction was completed, the reaction solution was filtered through Buchner funnel and concentrated to give a crude oil. Petroleum ether (12.8 L) was added to the crude product, and then stirred at 45° C. for 1 hour, slowly cooled to room temperature over about 1 hour, and filtered to give 1-(2,4-dibenzyloxyphenyl)ethanone (7 kg, yield of 87.4%, purity of 95.4%) as a milk-white solid. m/z 333 [M+H]$^+$.

Step 2:

The internal temperature was controlled between 0° C. and 40° C. under the protection of nitrogen, methylmagnesium bromide (3.0 mol, 8.61 L, 1.30 equivalents) was slowly added dropwise to a solution of 1-(2,4dibenzyloxyphenyl)ethanone (7.00 kg, 19.88 mol, 1.00 equivalent) in tetrahydrofuran (24 L), followed by stirring for further 0.5 hour at a temperature in the range of 0-40° C. After the reaction was completed, a saturated aqueous ammonium chloride solution (30 L) and aqueous ammonia (90 mL) were added dropwise to the reaction solution while the temperature was controlled between 25° C. and 40° C., diluted with ethyl acetate (10 L), and then the organic phase and aqueous phase were separated, and the aqueous phase was extracted with ethyl acetate (10 L) again. The organic phases were combined and dried over anhydrous sodium sulfate, filtered and concentrated to give a crude oil. The oil was allowed to stand for 16 hours to generate a solid, to which dichloromethane (50 L) was added, and then washed with saturated aqueous sodium bicarbonate solution (30 L), water (30 L) and saturated aqueous sodium chloride solution (30 L). The organic phase was dried over anhydrous sodium sulfate, and then filtered and concentrated to give 2-(2,4-dibenzyloxyphenyl)propan-2ol (7.00 kg, 17.62 mol, yield of 88.63%, purity of 87.7%) as a white solid, which was directly used in the next step. m/z 331 [M+H-18]$^+$.

Step 3:

At −70° C. and under the protection of nitrogen, trifluoroacetic acid (328.38 g, 2.88 mol, 213.23 ml, 2.00 equivalents) was slowly added dropwise into a solution of 2-(2, 4dibenzyloxyphenyl)propan-2ol (500.00 g, 1.44 mol, 1.00 equivalent) in dichloromethane (3.5 L) while the temperature was controlled between −65° C. and −68° C., and then stirred for 0.5 h. Triethylsilyl hydride (217.68 g, 1.87 mol, 298.19 mL, 1.30 equivalents) was slowly added dropwise while the temperature was controlled between −65° C. and −68° C., and after the completion of the dropwise addition, the reaction was stirred for 4 hours at −65° C. to −70° C. After the reaction was completed, saturated sodium bicarbonate (2.4 L) was added dropwise to the reaction solution over about 1 hour, and after the completion of the dropwise addition, the reaction was stirred for another 1 hour, extracted once with dichloromethane (2 L), and washed once with water (2 L). The organic phase was dried over anhydrous sodium sulfate, filtered and concentrated to give 2,4-benzyloxy-1-isopropyl-benzene (500 g, crude, purity of 86.8%) as a yellow crude oil, which was directly used in the next step. m/z 333 [M+H]$^+$.

Step 4:

At about 5° C., 2.53 kg of POCl$_3$ (2.53 kg, 16.48 mol, 1.63 equivalents) was added dropwise to 12 L of N,N-dimethylformamide, and the temperature was controlled within 15° C., and the addition was completed in about one hour. After being stirred for 30 minutes, the substrate of 2,4benzyloxy-1-isopropyl-benzene (3.36 kg, 10.11 mol, 1.00 equivalent) was added to the reaction solution. The reaction solution was dark red, and the reactor was heated to 80° C. and the stirring was continued for 2 hours. After the reaction was completed, the reaction mixture was added dropwise to sodium acetate aqueous solution (10 kg of sodium acetate/36 L of water) to give a bright yellow solid. The solid was filtered and respectively washed twice with water (10 L) and ethanol (10 L). The filter cake was taken out and concentrated under reduced pressure to give 2,4benzyloxy-5isopropyl-benzaldehyde (3.40 kg, 8.95 mol, yield of 88.53%, purity of 94.9%) as a white solid. m/z 361 [M+H]$^+$, 383 [M+Na]$^+$.

Step 5:

At room temperature, hydroxylamine hydrochloride (1.54 kg, 22.20 mol, 2.00 equivalents) and DIEA (2.15 kg, 16.65 mol, 2.91 L, 1.50 equivalents) were added to a solution of 2,4-benzyloxy-5-isopropyl-benzaldehyde (4.00 kg, 11.10 mol, 1.00 equivalent) in ethanol (30 L), and then heated to 80° C. and stirred for 3 hours. After the reaction was completed, the reaction solution was cooled to room temperature, and water (30 L) was added thereto. The mixture was stirred for 3 h, and then filtered, and the filter cake was washed twice with water (30 L) to give (1E)-2,4-benzyloxy-5-isopropyl-benzaldehyde oxime (5.8 kg, crude product, purity of 95%) as a crude white solid, which was directly used in the next step. m/z 376 [M+H]$^+$.

Step 6:

At 25° C., propargyl alcohol (1.49 kg, 26.63 mol, 1.57 L, 2.50 equivalents) was added to a solution of (1 E)-2,4-benzyloxy-5-isopropyl-benzaldehyde oxime (4 kg, 10.65 mol, 1.00 equivalent) in tetrahydrofuran (20 L), and slowly added dropwise with sodium hypochlorite solution (20 L), and the reaction solution was stirred at 25° C. for 12 hours. After the reaction was completed, the reaction solution was extracted by adding ethyl acetate (10 L), and the aqueous phase was extracted with ethyl acetate (20 L) once. The organic phases were combined, dried over anhydrous sodium sulfate, filtered and concentrated to give a black oil. The oil was dispersed by adding dichloromethane (5 L) and petroleum ether (15 L), then concentrated under reduced pressure to give [3-(2,4-dibenzyloxy-5-isopropyl-phenyl)isoxazol-5-yl]methanol (4.56 kg, 9.36 mol, yield of 87.90%, purity of 88.17%) as a crude yellow solid, which was directly used in the next step. m/z 430 [M+H]$^+$.

Step 7:

At 15° C., NIS (2.83 kg, 12.57 mol, 1.50 equivalents) and concentrated sulfuric acid (167.77 g, 1.68 mol, 91.18 ml, purity of 98%, 0.20 equivalents) were added to a solution of [3-(2,4-dibenzyloxy-5-isopropyl-phenyl)isoxazol-5-yl]methanol (4.00 kg, 8.38 mol, 1.00 equivalent) in acetonitrile (36 L), and the reaction solution was stirred at 15° C. for 4 hours. After the reaction was completed, the reaction solution was poured into a solution of sodium sulfite (1.06 kg) in water (20 L) and stirred for 1 hour. The reaction solution was extracted with ethyl acetate (10 L), and extracted once more with ethyl acetate (10 L). The organic phases were combined and washed with saturated saline solution (15 L) three times at each time. The organic phase was dried over anhydrous sodium sulfate, filtered and concentrated to give [3-(2,4-dibenzyloxy-5-isopropyl-phenyl)-4-iodo-isoxazol-5-yl]methanol (5.00 kg, crude product, purity of 71%) as a crude yellow solid, which was directly used in the next step. m/z 556 [M+H]$^+$.

Step 8:

At 9° C., TEMPO (70.95 g, 451.21 mmol, 0.07 equivalents), disodium hydrogen phosphate (0.4 M, 4.67 L, 0.29 equivalents) and sodium dihydrogen phosphate (0.4 M, 6.12 L, 0.38 equivalents) were added to a solution of [3-(2,4-dibenzyloxy-5-isopropyl-phenyl)-4-iodo-isoxazol-5-yl]methanol (5.00 kg, 6.45 mol, 1.00 equivalent) in acetonitrile (24 L). Then, a solution of sodium hypochlorite (1.71 kg, 16.11 mol, purity of 85%, 2.50 equivalents) in water (5.6 L) was added in four portions at a temperature not more than 40° C. over 2 hours, and a solution of sodium hypochlorite (287.90 g, 193.37 mmol, 237.93 mL, purity of 5%, 0.03 equivalents) in water (1.1 L) was added at the same time. The reaction solution was stirred at 30-35° C. for 3 hours. After the reaction was completed, the reaction solution was poured into a solution of sodium sulfite (1.95 kg) in water (12 L), and stirred for 12 h, and extracted with ethyl acetate (20 L). The organic phase was washed with saturated saline solution (15 L, twice), and finally dried over anhydrous sodium sulfate, filtered and concentrated under reduced pressure to give 3-(2,4-dibenzyloxy-5-isopropylphenyl)-4-iodo-isoxazole-5-carboxylic acid (3.95 kg, crude product, purity of 74.3%) as a yellow gel, which was directly used in the next step. m/z 570 [M+H]$^+$.

Step 9, Method 1: (acylating agent)

At 0° C., oxalyl chloride (2.17 kg, 17.13 mol, 1.50 L, 2.50 equivalents) and N,N-dimethylformamide (50.06 g, 685.00 mmol, 52.69 mL, 0.10 equivalents) were added to a solution of 3-(2,4-dibenzyloxy-5-isopropylphenyl)-4-iodo-isoxazole-5-carboxylic acid (3.90 kg, 6.85 mol, 1.00 equivalent) in dichloromethane (30 L). After the mixture was stirred at 0° C. for 1 hour, the reaction solution was concentrated under vacuum to give an intermediate. This intermediate was dissolved in a solution of dichloromethane (30 L), to which ethylamine (1.54 kg, 34.25 mol, 2.24 L, 5.00 equivalents) was added at 0° C. After being stirred at 0° C. for 1 hour, the mixture was poured into saturated sodium bicarbonate aqueous solution (30 L). Then the organic phase was washed with saturated sodium bicarbonate aqueous solution (30 L×3). The organic phase was dried over anhydrous sodium sulfate, filtered and concentrated under vacuum to give a crude product. Ethyl acetate (10 L) was added to the crude product, and then concentrated until it was almost dried completely, to which ethyl acetate (5 L) was added and then it was further concentrated to give a crude product (6.5 kg). Ethanol (3.5 L) was added thereto and stirred for 12 hours and filtered. The filter cake was washed with ethanol (1 L×2) to give 3-(2,4-dibenzyloxy-5-isopropylphenyl)-N-ethyl-4-iodo-isoxazole-5-carboxamide (1.30 kg, 2.05 mol, yield of 29.91%, purity of 94%) as a white solid product. m/z 597 [M+H]$^+$; $^1$H NMR (400 MHz, DMSO-d$_6$) δ=7.37 (m, 10H), 7.17 (s, 1H), 6.62 (m, 2H), 3.52 (td, 2H), 3.34 (m, 1H), 1.29 (t, 3H), 1.23 (d, 6H).

Step 9, Method 2: (condensation agent)

At 0° C., diisopropylethylamine (90.79 mg, 702.51 µmol, 122.69 µL, 2.00 equivalents) and bis(2-oxo-3-oxazolidinyl) phosphinic chloride (107.30 mg, 421.50 µmol, 1.20 equivalents) were added to a solution of 3-(2,4-dibenzyloxy-5-isopropylphenyl)-4-iodo-isoxazole-5-carboxylic acid (200.00 mg, 351.25 µmol, 1.00 equivalent) in N,N-dimethylformamide (5.00 mL). The mixture was stirred at 0° C. for 1 hour, and then ethylamine (47.50 mg, 1.05 mmol, 68.85 µL, 3.00 equivalents) was added to the reaction mixture at 0° C. The mixture was heated to 80° C. and stirred at 80° C. for 11 hours. The reaction solution was concentrated to give 3(2,4dibenzyloxy-5isopropylphenyl)-N-ethyl-4iodo-isoxazole-5-carboxamide (400 mg, crude product, purity of 30%) as a yellow oil. m/z 597 [M+H]$^+$.

Preparation of Compound 7:

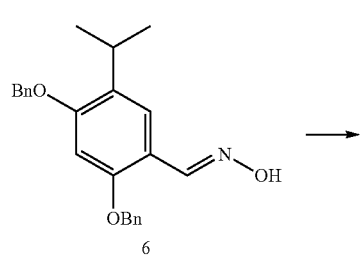

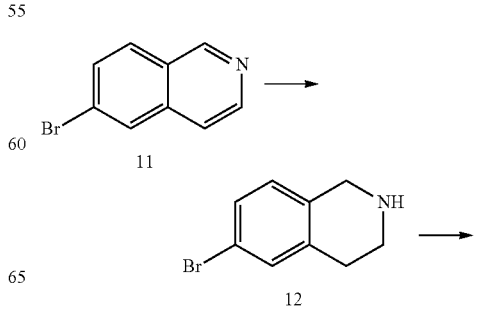

Step 1:

(1E)-2,4dibenzyloxy-5isopropyl-benzaldehyde oxime (8.50 g, 22.64 mmol, 1.00 equivalent) was added to dichloromethane (160 mL), and NCS (4.53 g, 33.96 mmol, 1.50 equivalents) was slowly added dropwise at 0° C. and stirred at this temperature for 2 hours. Then the reaction was slowly heated to 20° C. and further stirred for 10 hours. The reaction solution was concentrated under reduced pressure to give (1Z)-2,4dibenzyloxy-N-hydroxy-5isopropyl-benzimidoyl chloride (9.30 g, crude product) as a yellow crude oil, which was directly used in the next step. m/z 410 [M+H]$^+$.

Step 2:

At 20° C., (1Z)-2,4dibenzyloxy-N-hydroxy-5isopropyl-benzimidoyl chloride (9.30 g, 22.69 mmol, 1.00 equivalent) and propargyl alcohol (1.91 g, 34.03 mmol, 1.50 equivalents) were added to toluene (100 mL), to which triethylamine (2.53 g, 24.96 mmol, 1.10 equivalents) was slowly added. The reaction solution was stirred at 20° C. for 12 hours. After the reaction was completed, water (50 mL) was added to the reaction solution, and it was extracted with ethyl acetate (25 mL×3). The organic phases were combined and washed with saturated saline solution (25 mL×2), and then dried over anhydrous sodium sulfate, filtered and concentrated under reduced pressure to give a crude product. The crude product was isolated and purified by silica gel column (100-200 mesh, PE/EA=20/1-4/1) to give [3(2,4-dibenzyloxy-5-isopropyl-phenyl)isoxazol-5-yl]methanol (3.80 g, 8.85 mmol, yield of 38.99%) as a yellow oil. m/z 430 [M+H]$^+$.

Preparation of the compound of formula (I):

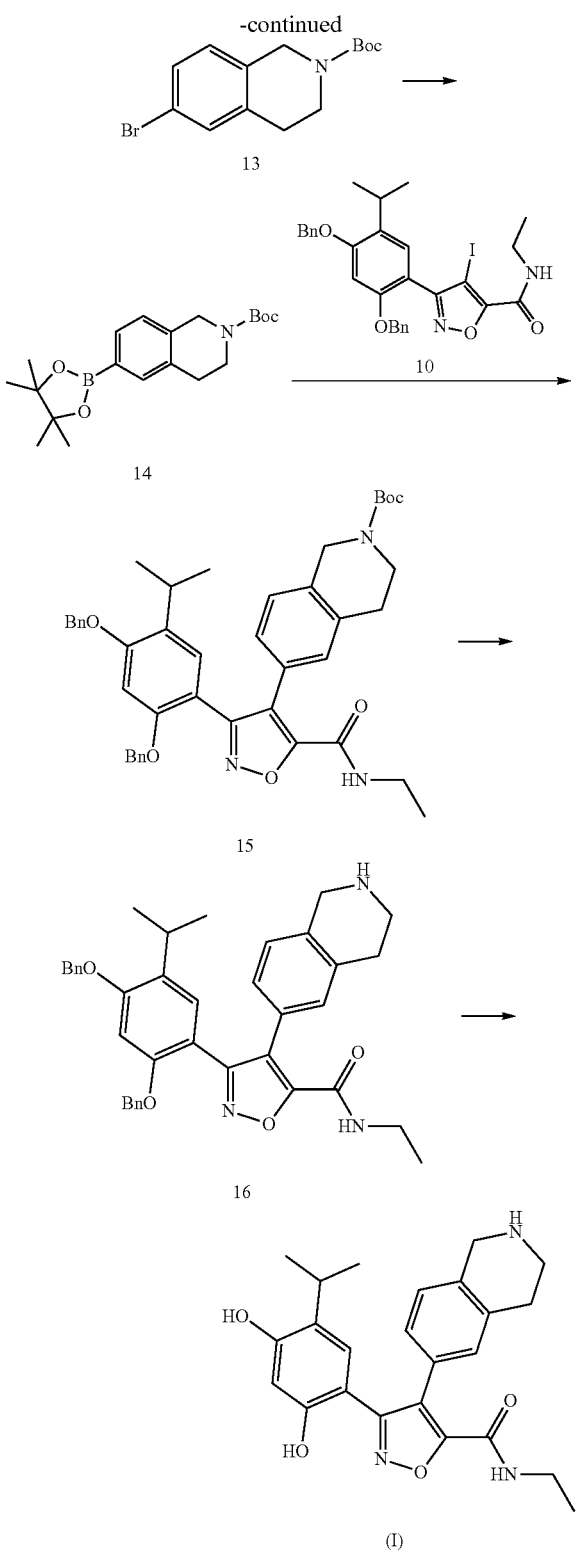

Step 1:

25 L of melted glacial acetic acid and 2.5 L of water were added to a 50 L reactor, and 6-bromoisoquinoline (2.5 kg, 12.02 mol, 1.00 equivalent) was added to the reactor. The reaction temperature was adjusted to 10° C. At 10-15° C., 1.43 kg of sodium borohydride was added in portions, and after feeding was finished over 7 hours, it was further stirred for 2 hours. After the reaction was completed, the reaction solution was slowly added dropwise to a solution of sodium hydroxide (17.5 kg) in water (87.5 L) at 5-15° C. After the completion of the dropwise addition, the mixture was stirred at room temperature for 10 hours, and filtered to give 6-bromo-1,2,3,4tetrahydroisoquinoline (8 kg, watercontaining crude product, purity of 95%) as a white solid, which was directly used in the next step. m/z 212, 214 (1:1) [M+H]$^+$.

Step 2:

Sodium bicarbonate (1.21 kg) and Boc$_2$O (2.62 kg) were added to a solution of 6-bromo-1,2,3,4tetrahydroisoquinoline (2.55 kg, 12.02 mol, 1.00 equivalent) in ethyl acetate (12.5 L) and water (12.5 L) at 20° C., and the reaction solution was stirred at 20° C. for 12 hours. After the reaction was completed, the reaction mixture was allowed to stand for layering, and the aqueous phase was extracted again with ethyl acetate (10 L×2). The organic phases were combined and washed once with water (10 L), dried over anhydrous sodium sulfate, filtered and concentrated to give N-tert-butoxycarbonyl-6bromo-1,2,3,4-tetrahydroisoquinoline (3.5 kg, 11.21 mol, yield of 91.4%, purity of 98%) as a yellow oil. m/z 256, 258 (1:1) [M+H-56]$^+$; $^1$H NMR (400 MHz, CDCl$_3$) δ=7.29 (m, 2H), 6.98 (d, 1H), 4.51 (s, 2H), 3.63 (t, 2H), 2.81 (t, 2H), 1.49 (s, 9H).

Step 3:

Bis(pinacolato)diboron (975 g) and KOAc (940 g) were added to a solution of N-tert-butoxycarbonyl-6bromo-1,2,3,4-tetrahydroisoquinoline (1 kg) in dioxane (10 L) under the protection of nitrogen at 25° C., to which the catalyst Pd(dppf)Cl$_2$ (13 g) was subsequently added. The mixture was stirred at 25° C. for 10 min, and then heated to 80° C. and stirred for 12 hours. After the reaction was completed, the mixture was filtered through diatomite put on Buchner funnel, rinsed with ethyl acetate (2.5 L×2), and the filtrate was concentrated to give N-tert-butoxycarbonyl-6-(4,4,5,5tetramethyl-1,3,2-dioxaborolan-2-yl)-1,2,3,4-tetrahydroisoquinoline (2.04 kg, crude product, purity of 85%) as a black crude oil, which was directly used in the next step. m/z 304 [M+H-56]$^+$.

Step 4:

Potassium carbonate (1.31 kg) and Pd(PPh$_3$)$_2$Cl$_2$ (69.6 g) were added to a solution of crude N-tert-butoxycarbonyl-6 (4,4,5,5tetramethyl-1,3,2dioxaborolan-2-yl)-1,2,3,4tetrahydroisoquinoline (1.15 kg, 3.2 mol, 1.00 equivalent) and 3(2,4-dibenzyloxy-5-isopropylphenyl)-N-ethyl-4iodo-isoxazole-5-carboxamide (2 kg, 3.2 mol, 1.00 equivalent) in DMF (20 L) and water (4 L) under the protection of nitrogen at 25° C. The mixture was stirred at 25° C. for 10 minutes, and then heated to 60° C. and stirred for 12 hours. After the reaction was completed, the mixture was cooled to 25° C., and the mixture was added to aqueous hydrochloric acid solution (0.4 mol, 30 L). Solid was precipitated, spin-dried with a centrifuge, washed with water (15 L×2), and then spin-dried to give tert-butyl 6(3-(2,4-dibenzyloxy-5-isopropyl-phenyl)-5-(ethylcarbamoyl)isoxazol-4-yl)-1,2,3,4-tetrahydroisoquinoline-2carboxylate (2.32 kg, crude product, purity of 75%) as a crude black solid, which was directly used in the next step. m/z 702 [M+H]$^+$.

Step 5:

At room temperature, a solution of hydrogen chloride in ethyl acetate (4 mol, 5 L) was slowly added dropwise to a solution of tert-butyl 6-(3-(2,4dibenzyloxy-5-isopropyl-phenyl)-5(ethylcarbamoyl)isoxazol-4-yl)-1,2,3,4-tetrahydroisoquinoline-2carboxylate (2.21 kg, 3.15 mol, 1.00 equivalent) in methyl tert-butyl ether (5 L), and the temperature was not more than 25° C. The mixture was stirred at room temperature for 12 hours. After the reaction was completed, the mixture was filtered through Buchner funnel to give the hydrochloride of the product, and the filter cake was washed with EA/MTBE=1/1 (2.5 L×2). The crude product was dissolved in a solution of DCM/MeOH=10/1 (17.6 L), and a solution of sodium carbonate (800 g) in water (16 L) was added to the organic phase and stirred for 1 hour. The solution was separated, and the organic phase was sequentially washed with an aqueous hydrochloric acid solution (0.3 mol/L, 17.6 L), an aqueous hydrochloric acid solution (0.1 mol/L, 17.6 L), a solution of sodium carbonate (800 g) in water (17.6 L) and a solution of sodium chloride (4 kg) in water (16 L). Finally, the mixture was dried over anhydrous sodium sulfate, and filtered and concentrated to give 3-(2,4-dibenzyloxy-5-isopropylphenyl)-N-ethyl-4(1,2,3,4-tetrahydroisoquinolin-6-yl)isoxazole-5-carboxamide (1.44 kg, crude product, purity of 90%) as a brown oil, which was directly used in the next step. m/z 602 $[M+H]^+$.

Step 6:

A solution of boron trichloride in dichloromethane (18.5 L, 1 mol of DCM solution) was slowly added to a solution of 3-(2,4-dibenzyloxy-5-isopropylphenyl)-N-ethyl-4(1,2,3,4tetrahydroisoquinolin-6-yl)isoxazole-5-carboxamide (1.44 kg, 2.39 mol, 1.00 equivalent) in dichloromethane (63 L) under the protection of nitrogen at −10° C. After being further stirred at 0° C. for 1 hour, the reaction mixture was heated to room temperature and stirred for 2 hours. The reaction solution was cooled to −10° C., and then the reaction was quenched by adding methanol (18 L). The reaction mixture was concentrated under vacuum to give a crude product. The crude product was slurried with dichloromethane/acetone=1/1 (14 L), filtered through Buchner funnel, and the filter cake was washed with dichloromethane/acetone=1/1 (1 L×2) to give a hydrochloride. 3-(2,4-dihydroxy-5-isopropylphenyl)-N-ethyl-4-(1,2,3,4tetrahydroisoquinolin-6-yl)isoxazole-5-carboxamide hydrochloride (747 g) was obtained as a yellow solid. 3(2,4dihydroxy-5isopropylphenyl)-N-ethyl-4-(1,2,3,4tetrahydroisoquinolin-6-yl)isoxazole-5-carboxamide hydrochloride (560 g) was added to a solution of dichloromethane/methanol=6/1 (36 L), and then added to a solution of sodium bicarbonate (500 g) in water (5 L) and stirred at room temperature for 1 hour. The solution was separated, and the aqueous phase was extracted with dichloromethane/methanol=7/1 (10 L×2). The organic phases were combined, dried over anhydrous sodium sulfate, filtered and concentrated to give a crude product (480 g). At 80° C., the solid crude product was completely dissolved in tetrahydrofuran (9 L), and tetrahydrofuran (5 L) was distilled off under atmospheric pressure. Then, it was slowly cooled to room temperature and stirred for 12 hours, cooled to 0° C. and stirred for 2 hours, and filtered. The filter cake was washed with iced tetrahydrofuran (500 mL×2) to give 3(2,4dihydroxy-5-isopropylphenyl)-N-ethyl-4-(1,2,3,4-tetrahydroisoquinolin-6-yl)isoxazole-5-carboxamide (432 g, yield of 42%, purity of 98.8%) as a white solid. m/z 422 $[M+H]^+$; $^1H$ NMR (400 MHz, DMSO-$d_6$) δ=9.51 (d, 2H), 8.85 (t, 1H), 6.94 (m, 3H), 6.84 (m, 1H), 6.33 (s, 1H), 3.76 (s, 2H), 3.22 (m, 2H), 3.04 (m, 1H), 2.86 (m, 2H), 2.54 (m, 2H), 1.08 (t, 3H), 1.04 (d, 6H).

EXAMPLE 2

Preparation of Various Crystals of the Compound of Formula (I)

Preparation of the A-type crystal:
Method 1:

20 g of the compound of formula (I) was taken, to which 400 mL of tetrahydrofuran was added, and stirred at 80° C. for about 1 hour until it was completely dissolved. Then, it was cooled to 40° C., and distilled to 100 mL under atmospheric pressure at 40° C. The reaction mixture was naturally cooled to 15-30° C. with stirring, and then stirred at 15-30° C., 12 hours in total. The solid was collected by filtration, and the solid was rinsed twice with 20 mL of tetrahydrofuran, and dried under vacuum at 40-45° C. to give 13 g of a white solid. After identification by XRPD, the solid crystal was A-type crystal.

Method 2:

54 g of the compound of formula (I) was taken, to which 1100 mL of tetrahydrofuran was added, and stirred at 70° C. until it was completely dissolved. Then, it was cooled to 40° C., and distilled to 300 mL under atmospheric pressure at 40° C. The reaction mixture was naturally cooled to 15-30° C. with stirring, and then stirred at 15-30° C., 12 hours in total. The solid was collected by filtration, and the solid was rinsed twice with 50 mL of tetrahydrofuran, and dried under vacuum (40-45° C.) to give a product (45 g). 450 mL of water was added to the product, and it was stirred at 60-80° C. for 6 hours. The reaction mixture was naturally cooled to 15-30° C. with stirring, and then stirred at 15-30° C., 12 hours in total. The solid was collected by filtration, and the solid was rinsed twice with water (90 mL) and dried under vacuum at 40-45° C. to give a white solid (38 g). After identification by XRPD, the solid crystal was A-type crystal.

Method 3:

35 g of the compound of formula (I) was taken, to which 700 mL of ethanol was added, and stirred at 80° C. until it was completely dissolved. Then at 80° C., 35 mL of water was added dropwise to the solution. The reaction mixture was naturally cooled to 15-30° C. with stirring, and then stirred at 15-30° C., 12 hours in total. The solid was collected by filtration, and the solid was rinsed twice with 70 mL of ethanol, and dried under vacuum at 40-45° C. to give 10 g of a white solid. After identification by XRPD, the solid crystal was A-type crystal.

Method 4:

5 g of the compound of the formula (I) was taken, to which 50 mL of acetone was added, and stirred at 15-30° C. for 12 hours. The solid was collected by filtration, and the solid was rinsed twice with 10 mL of acetone, dried under vacuum (40-45° C.) to give 4 g of a white solid. After identification by XRPD, the solid crystal was A-type crystal.

Method 5:

50 mg of the compound of formula (I) was taken, to which 0.35 mL of methanol was added, stirred at 40° C. for 2 days, and then centrifuged. The solid was collected by filtration, and dried in a vacuum drying oven (30° C.) overnight to give a white solid. After identification by XRPD, the solid crystal was A-type crystal.

Method 6:

50 mg of the compound of formula (I) was taken, to which 0.35 mL of ethanol was added, stirred at 40° C. for 2 days, and then centrifuged. The solid was collected by filtration and dried in a vacuum drying oven (30° C.) overnight to give a white solid. After identification by XRPD, the solid crystal was A-type crystal.

Method 7:

50 mg of the compound of formula (I) was taken, to which 0.35 mL of isopropanol was added, stirred at 40° C. for 2 days, and then centrifuged. The solid was collected by filtration and dried in a vacuum drying oven (30° C.) overnight to give a white solid. After identification by XRPD, the solid crystal was A-type crystal.

Method 8:

50 mg of the compound of formula (I) was taken, to which 0.35 mL of acetone was added, stirred at 40° C. for 2 days, and then centrifuged. The solid was collected by filtration and dried in a vacuum drying oven (30° C.) overnight to give a white solid.

After identification by XRPD, the solid crystal was A-type crystal.

Method 9:

50 mg of the compound of formula (I) was taken, to which 0.35 mL of tetrahydrofuran was added, stirred at 40° C. for 2 days, and then centrifuged. The solid was collected by filtration and dried in a vacuum drying oven (30° C.) overnight to give a white solid. After identification by XRPD, the solid crystal was A-type crystal.

Method 10:

50 mg of the compound of formula (I) was taken, to which 0.35 mL of 1,4-dioxane was added, stirred at 40° C. for 2 days, and then centrifuged. The solid was collected by filtration and dried in a vacuum drying oven (30° C.) overnight to give a white solid. After identification by XRPD, the solid crystal was A-type crystal.

Method 11:

50 mg of the compound of formula (I) was taken, to which 0.35 mL of methanol:water=3:1 was added, stirred at 40° C. for 2 days, and then centrifuged. The solid was collected by filtration and dried in a vacuum drying oven (30° C.) overnight to give a white solid. After identification by XRPD, the solid crystal was A-type crystal.

Method 12:

50 mg of the compound of formula (I) was taken, to which 0.35 mL of ethanol:water=3:1 was added, stirred at 40° C. for 2 days, and then centrifuged. The solid was collected by filtration and dried in a vacuum drying oven (30° C.) overnight to give a white solid. After identification by XRPD, the solid crystal was A-type crystal.

Method 13:

50 mg of the compound of formula (I) was taken, to which 0.35 mL of acetonitrile:water=3:1 was added, stirred at 40° C. for 2 days, and then centrifuged. The solid was collected by filtration and dried in a vacuum drying oven (30° C.) overnight to give a white solid. After identification by XRPD, the solid crystal was A-type crystal.

Method 14:

50 mg of the compound of formula (I) was taken, to which 0.35 mL of isopropanol:water=3:1 was added, stirred at 40° C. for 2 days, and then centrifuged. The solid was collected by filtration and dried in a vacuum drying oven (30° C.) overnight to give a white solid. After identification by XRPD, the solid crystal was A-type crystal.

Preparation of B-type crystal:

About 35 mg of the compound of formula (I) was taken, to which 1.5 mL of tetrahydrofuran was added. Ultrasound was used for dissolution, and 6 mL of anti-solvent water was added with stirring. The precipitated solid sample was dried in a vacuum drying oven (40° C.) overnight to give a white solid. After identification by XRPD, the solid crystal was B-type crystal.

Preparation of C-type crystal:

About 35 mg of the compound of formula (I) was taken, to which 1.5 mL of tetrahydrofuran was added. Ultrasound was used for dissolution, and 7 mL of anti-solvent methyl tert-butyl ether was added with stirring. The precipitated solid sample was dried in a vacuum drying oven (40° C.) overnight to give a white solid. After identification by XRPD, the solid crystal was C-type crystal.

Preparation of D-type crystal:

About 35 mg of the compound of formula (I) was taken, to which 5 mL of 2-butanone was added. Ultrasound was used for dissolution, and 5 mL of anti-solvent n-heptane was added with stirring. The precipitated solid sample was dried in a vacuum drying oven (40° C.) overnight to give a white solid. After identification by XRPD, the solid crystal was D-type crystal.

TABLE 1

XRPD analysis data for A-type crystal of the compound of formula (I)

| No. | 2θ angle (°) | Interplanar spacing (Å) | Relative intensity (%) |
|---|---|---|---|
| 1 | 10.664 | 8.289 | 100 |
| 2 | 11.413 | 7.7468 | 11.9 |
| 3 | 12.66 | 6.9865 | 3.1 |
| 4 | 13.482 | 6.5622 | 2.6 |
| 5 | 15.085 | 5.8684 | 23.6 |
| 6 | 15.841 | 5.5899 | 5.2 |
| 7 | 16.364 | 5.4124 | 3.7 |
| 8 | 17.476 | 5.0706 | 3.5 |
| 9 | 17.85 | 4.9651 | 11 |
| 10 | 18.219 | 4.8653 | 6.8 |
| 11 | 18.709 | 4.7389 | 1 |
| 12 | 19.165 | 4.6271 | 33.4 |
| 13 | 19.596 | 4.5263 | 11.5 |
| 14 | 20.193 | 4.3939 | 4.7 |
| 15 | 20.43 | 4.3435 | 12.6 |
| 16 | 20.744 | 4.2783 | 4.9 |
| 17 | 21.332 | 4.1619 | 2 |
| 18 | 21.808 | 4.072 | 10.7 |
| 19 | 22.186 | 4.0035 | 15.1 |
| 20 | 22.857 | 3.8874 | 9.7 |
| 21 | 23.091 | 3.8485 | 5.9 |
| 22 | 23.614 | 3.7646 | 1.6 |
| 23 | 23.844 | 3.7288 | 1.8 |
| 24 | 24.567 | 3.6205 | 4.3 |
| 25 | 25.24 | 3.5256 | 2.3 |
| 26 | 25.756 | 3.4561 | 19.1 |
| 27 | 26.051 | 3.4176 | 7.5 |
| 28 | 27.153 | 3.2814 | 4.2 |
| 29 | 27.748 | 3.2123 | 6.8 |
| 30 | 28.455 | 3.1341 | 2.2 |
| 31 | 29.641 | 3.0114 | 2.3 |
| 32 | 30.739 | 2.9062 | 2 |
| 33 | 32.083 | 2.7875 | 2.3 |

TABLE 2

XRPD analysis data for B-type crystal of the compound of formula (I)

| No. | 2θ angle (°) | Interplanar spacing (Å) | Relative intensity (%) |
|---|---|---|---|
| 1 | 7.339 | 12.0351 | 100 |
| 2 | 12.233 | 7.2294 | 2.1 |
| 3 | 12.527 | 7.0605 | 3.4 |
| 4 | 14.685 | 6.0271 | 8.9 |
| 5 | 17.036 | 5.2003 | 0.7 |
| 6 | 18.196 | 4.8715 | 0.7 |
| 7 | 18.716 | 4.7371 | 1.5 |
| 8 | 19.026 | 4.6607 | 2.6 |
| 9 | 19.539 | 4.5395 | 0.6 |
| 10 | 20.668 | 4.294 | 4.2 |
| 11 | 22.149 | 4.01 | 6.1 |

TABLE 3

XRPD analysis data for C-type crystal of the compound of formula (I)

| No. | 2θ angle (°) | Interplanar spacing (Å) | Relative intensity (%) |
|---|---|---|---|
| 1 | 6.449 | 13.6932 | 100 |
| 2 | 7.676 | 11.5081 | 88.8 |
| 3 | 10.08 | 8.7677 | 3.3 |
| 4 | 10.557 | 8.3728 | 39.7 |
| 5 | 12.908 | 6.8528 | 91.5 |
| 6 | 13.578 | 6.5161 | 90.4 |
| 7 | 14.092 | 6.2794 | 2.9 |
| 8 | 15.395 | 5.7508 | 45.2 |
| 9 | 16.72 | 5.2981 | 9.9 |
| 10 | 17.786 | 4.9828 | 9.6 |
| 11 | 18.298 | 4.8445 | 12 |
| 12 | 18.753 | 4.7278 | 1.6 |
| 13 | 19.409 | 4.5696 | 2.4 |
| 14 | 19.717 | 4.4988 | 3.2 |
| 15 | 21.141 | 4.199 | 31.6 |
| 16 | 21.636 | 4.104 | 6.6 |
| 17 | 23.157 | 3.8378 | 17.1 |
| 18 | 25.744 | 3.4577 | 20 |
| 19 | 26.317 | 3.3837 | 55.4 |
| 20 | 29.953 | 2.9807 | 2.6 |
| 21 | 32.872 | 2.7224 | 3.4 |
| 22 | 33.702 | 2.6572 | 4.2 |
| 23 | 35.087 | 2.5555 | 2.4 |
| 24 | 39.43 | 2.2834 | 2.9 |

TABLE 4

XRPD analysis data for D-type crystal of the compound of formula (I)

| No. | 2θ angle (°) | Interplanar spacing (Å) | Relative intensity (%) |
|---|---|---|---|
| 1 | 5.955 | 14.8283 | 100 |
| 2 | 7.497 | 11.7815 | 3.2 |
| 3 | 9.53 | 9.2726 | 27.4 |
| 4 | 9.649 | 9.1583 | 21.1 |
| 5 | 10.576 | 8.3577 | 1.9 |
| 6 | 11.939 | 7.4069 | 17.7 |
| 7 | 12.455 | 7.1008 | 6.6 |
| 8 | 13.873 | 6.378 | 4.4 |
| 9 | 14.427 | 6.1343 | 14 |
| 10 | 14.92 | 5.9326 | 9.4 |
| 11 | 16.423 | 5.3932 | 13.5 |
| 12 | 17.352 | 5.1064 | 7.2 |
| 13 | 17.567 | 5.0442 | 5.4 |
| 14 | 19.148 | 4.6313 | 9.5 |
| 15 | 19.425 | 4.5659 | 45.4 |
| 16 | 20.255 | 4.3806 | 6 |
| 17 | 20.507 | 4.3273 | 3.3 |
| 18 | 21.182 | 4.191 | 1.8 |
| 19 | 22.009 | 4.0354 | 22.9 |
| 20 | 22.367 | 3.9715 | 5.7 |
| 21 | 22.684 | 3.9167 | 2.1 |
| 22 | 23.061 | 3.8535 | 7.6 |
| 23 | 23.694 | 3.7519 | 5 |
| 24 | 24.064 | 3.6951 | 3 |
| 25 | 24.563 | 3.6212 | 5.1 |
| 26 | 25.113 | 3.5431 | 3.9 |
| 27 | 25.487 | 3.4919 | 14.1 |
| 28 | 25.822 | 3.4474 | 5.1 |
| 29 | 27.147 | 3.2821 | 9 |
| 30 | 28.356 | 3.1449 | 3.2 |
| 31 | 28.69 | 3.109 | 2 |
| 32 | 29.085 | 3.0677 | 1.1 |
| 33 | 29.396 | 3.0359 | 1.8 |
| 34 | 30.761 | 2.9042 | 4.5 |
| 35 | 32.813 | 2.7272 | 1.7 |
| 36 | 33.263 | 2.6913 | 2 |
| 37 | 33.663 | 2.6602 | 3.5 |
| 38 | 36.427 | 2.4644 | 2.2 |

EXAMPLE 3

Study on Salt Formation of the Compound of Formula (I)

About 84 mg of the compound of formula (I) was weighed, added to an 8 mL vial, dissolved by adding 3 mL of THF and heating to 50° C., to which 17.5 µL of hydrochloric acid (diluted 10 times with THF, slowly added in its corresponding volume) was then slowly added. Phenomenon was observed. It was stirred at 25° C. overnight. The sample with the generated precipitates was quickly centrifuged to obtain a salt-forming product.

About 84 mg of the compound of formula (I) was weighed, added to an 8 mL vial, dissolved by adding 3 mL of THF and heating to 50° C., to which 11.4 µL of sulfuric acid (diluted 10 times with THF, slowly added in its corresponding volume) was then slowly added. Phenomenon was observed. It was stirred at 25° C. overnight. The sample with the generated precipitates was quickly centrifuged to obtain a salt-forming product.

About 84 mg of the compound of formula (I) was weighed, added to an 8 mL vial, dissolved by adding 3 mL of THF and heating to 50° C., to which 13.6 µL of methanesulfonic acid (diluted 10 times with THF, slowly added in its corresponding volume) was then slowly added. Phenomenon was observed. It was stirred at 25° C. overnight. The sample with the generated precipitates was quickly centrifuged to obtain a salt-forming product.

About 84 mg of the compound of formula (I) was weighed, added to an 8 mL vial, dissolved by adding 3 mL of THF and heating to 50° C., to which 40.12 mg of p-toluenesulfonic acid (2 times the weight of it was weighed and dissolved in 1m L of THF, and 500 µL of the resulting solution was taken and added slowly) was then slowly added. Phenomenon was observed. It was stirred at 25° C. overnight. The sample with the generated precipitates was quickly centrifuged to obtain a salt-forming product.

About 84 mg of the compound of formula (I) was weighed, added to an 8 mL vial, dissolved by adding 3 mL of THF and heating to 50° C., to which 24.52 mg of maleic acid (2 times the weight of it was weighed and dissolved in 1mL of THF, and 500 µL of the resulting solution was taken and added slowly) was then slowly added. Phenomenon was observed. It was stirred at 25° C. overnight. The sample with the generated precipitates was quickly centrifuged to obtain a salt-forming product.

About 84 mg of the compound of formula (I) was weighed, added to an 8 mL vial, dissolved by adding 3 mL of THF and heating to 50° C., to which 40.07 mg of citric acid (2 times the weight of it was weighed and dissolved in 1mL of THF, and 500 µL of the resulting solution was taken and added slowly) was then slowly added. Phenomenon was observed. It was stirred at 25° C. overnight. No precipitate appeared. N-heptane was added until precipitate appeared, and the sample was quickly centrifuged to obtain a salt-forming product.

About 84 mg of the compound of formula (I) was weighed, added to an 8 mL vial, dissolved by adding 3 mL of THF and heating to 50° C., to which 31.45 mg of L(+)-tartaric acid (2 times the weight of it was weighed and dissolved in 1mL of THF, and 500 µL of the resulting solution was taken and added slowly) was then slowly added. Phenomenon was observed. It was stirred at 25° C. overnight. No precipitate appeared. N-heptane was added until precipitate appeared, and the sample was quickly centrifuged to obtain a salt-forming product.

About 84 mg of the compound of formula (I) was weighed, added to an 8 mL vial, dissolved by adding 3 mL of THF and heating to 50° C., to which 84 mg of API (2 times the weight of it was weighed and dissolved in 1m L of THF, and 500 μL of the resulting solution was taken and added slowly) was then slowly added. Phenomenon was observed. It was stirred at 25° C. overnight. No precipitate appeared. N-heptane was added until precipitate appeared, and the sample was quickly centrifuged to obtain a salt-forming product.

EXAMPLE 4

Solubility Test of the Compound of Formula (I)

Test purposes:
The solubilities of the A-type crystal of the compound of formula (I) and various salts thereof under different conditions were determined, so as to develop crystal, salt and dissolution system with the optimal solubility for the compound.

Test materials:
Hydrochloric acid, acetic acid, sodium acetate, sodium chloride, 5% glucose solution, water (buffer is a buffer solution of acetic acid/sodium acetate).

Test method:
2 mg of a sample was weighed, and dissolved by adding a solvent (10 μL) thereto at room temperature. Whether the raw material was dissolved was observed: if the raw material was completely dissolved, the solubility (2 mg/solvent volume) was calculated; if the raw material was not completely dissolved, the solvent was added in portions, 10 μL of the solvent per time, until the raw material was completely dissolved, and the solubility was calculated. The total amount of the added solvents was up to 2 mL. If the total amount of the added solvents reached 2 mL and the raw material was still not completely dissolved, the solubility of the raw material in the solvent was defined as being less than 1 mg/mL.

Test results:
The test results of the rough solubility for the compounds of formula (I) were shown in Table 5.

Conclusions:
The compound of formula (I) has a higher solubility in the buffer of pH 3.5-4.5, and the hydrochloride and methanesulfonate of the compound have significantly higher solubilities than that of the A-type crystal of the compound.

TABLE 5

Test results of the rough solubility for the compounds of formula (I)

| solvent | Approximate solubility (mg/mL)* | | | |
|---|---|---|---|---|
| | A-type crystal | hydrochloride | methanesulfonate | maleate |
| water | <1 | 5.3-6.3 | 6.3-8.6 | 2.2-2.6 |
| 0.9% NaCl solution | <1 | <2 | <2 | <2 |
| 5% glucose solution | <1 | 4.6-5.5 | 6.5-8.7 | 2.1-2.3 |
| pH 3.5 buffer | 80-100 | 9.5-14.2 | 43.5-65.3 | 6.5-7.5 |
| pH 4.5 buffer | 30-50 | 5.8-7.3 | 17.6-26.4 | 3.4-3.9 |
| pH 5.5 buffer | <1 | <2 | <2 | <2 |
| pH 6.5 buffer | <1 | N/A | N/A | N/A |
| pH 7.5 buffer | <1 | <2 | <2 | <2 |
| pH 6.8 buffer | <1 | <2 | <2 | <2 |
| 0.1N HCl | <1 | N/A | N/A | N/A |
| 0.01N HCl | 0.8-1 | N/A | N/A | N/A |

EXAMPLE 5

Study on Tissue Distribution of the Compound of Formula (I)

1. Summary
SD rats were used as test animals, and the drug concentrations in plasma, lung and breast tissues of rats at different times after administrating the compound of formula (I) via the injection in tail vein were measured by using LC/MS/MS method. The tissue distribution of the compound of the present invention in rats was investigated, and pharmacokinetic characteristics thereof were evaluated.

2. Test protocol
2.1 Test drugs:
Luminespib, Ganetespib and the compound of formula (I).

2.2 Test animals:
100-200 g of healthy adult male SD rats, 9 in total, purchased from Shanghai SLAC Laboratory Animal Co., Ltd.

2.3 Drug formulation:
Appropriate amounts of samples were weighed, and Luminespib, Ganetespib and the compound of formula (I) of the present invention were respectively formulated into a clear solution with a concentration of 2.5 mg/mL for intravenous injection, wherein the solvent was consisted of 10% (v/v) of DMSO, 14% (v/v) of polyoxyethylene hydrogenated castor oil 40, and 76% (v/v) of 5% aqueous glucose solution.

2.4 Administration:
9 SD male rats were divided into three groups, three rats per group. The rats were administered intravenously through tail vein at a dose of 1 mg/kg after being normally fed.

3. Operation
Samples of blood, lung and breast tissues were collected from the rats in three groups at 0.5, 6, and 24 hours after administration, respectively. The blood sample was separated by centrifugation at 4° C., 3000 rpm/min for 15 min within half an hour after collection, so as to obtain plasma sample. The resulting plasma sample was deposited in polypropylene tubes and stored at −80° C. for LC/MS/MS analysis. After blood sample was collected, the animals were sacrificed with $CO_2$, and the tissue samples were collected. Each tissue sample was washed twice with cold deionized water and adhered onto filter paper. Each tissue sample was then homogenized several times in MeOH/15 mM PBS (1:2) (5 mL MeOH/15 mM PBS (1:2) per gram of tissue, with dilution coefficient of 6), to ensure the formation of homogeneous phase. The whole process was carried out at a freezing point temperature. The homogenized samples were quickly frozen by using dry ice and stored at −80° C. for bioassay.

The contents of the test compounds in the plasma, lung and breast tissues of the rats after the administration by injection were measured with LC/MS/MS method.

4. Pharmacokinetic parameter results
See Table 6.

TABLE 6

Tissue distribution results of the compound of formula (I)

| Tissue | Time (h) | Luminespib | Ganetespib | Compound of formula (I) |
|---|---|---|---|---|
| Plasma concentration (nM) | 0.5 | 67.1 | 267 | 115 |
| | 6 | ND | 4.46 | 9.98 |
| | 24 | ND | ND | 3.72 |

TABLE 6-continued

Tissue distribution results of the compound of formula (I)

| Tissue | Time (h) | Luminespib | Ganetespib | Compound of formula (I) |
|---|---|---|---|---|
| Plasma exposure (nM · h) | | ND | ND | 415 |
| Lung concentration (nM) | 0.5 | 1002 | 1010 | 3036 |
| | 6 | 257 | 101 | 1534 |
| | 24 | 35.9 | ND | 613 |
| Lung exposure (nM · h) | | 5284 | ND | 30933 |
| Breast tissue concentration (nM) | 0.5 | 104 | 352 | 395 |
| | 6 | 61.4 | 70.9 | 376 |
| | 24 | ND | ND | 199 |
| Breast tissue exposure (nM · h) | | ND | ND | 7226 |

Note:
ND indicates beyond the detection limit of the instrument, and no relevant data were detected.

5. Conclusions

When the compound of formula (I) was administered at an injection dose of 1 mg/kg, the blood concentrations in the lung and breast tissues of rats were significantly higher compared with Luminespib and Ganetespib at the same dose, and the tissue exposures were also significantly greater, indicating that the compound of formula (I) has better application prospects in cancers such as lung cancer and breast cancer and the like.

EXAMPLE 6

In Vivo Pharmacodynamic Evaluation of the Compound of Formula (I) in Animals with Breast Cancer BT-474 tumor cells were subcutaneously inoculated into the right axillary fossa of nude mice at $5 \times 10^6$/mouse to form transplanted tumors. When the volume thereof reached 100-200 mm³, the animals were randomly grouped based on tumor volumes: 6 mice in negative control group; 6 mice in positive control group; and 6 mice in each test group. The mice in the treatment groups were intravenously injected with different concentrations of positive drug Ganetespib (20 mg/kg) and the compound of formula (I) (10 mg/kg and 20 mg/kg) three times a week, and the mice in the negative control group were administrated with equal amount of vehicles at the same time. The length (A) and width (B) of the tumor were measured twice a week by using a vernier caliper, and the tumor volume $V = A \times B^2/2$ was thereby calculated. The calculation of relative tumor volume (RTV) follows: $RTV = V_t/V_0$, wherein $V_t$ was the tumor volume at the end of administration, and $V_0$ was the tumor volume measured before administration to each cage. The pharmacodynamic evaluation index of antitumor activity was the relative tumor proliferation rate T/C (%), and the calculation formula was: T/C (%) = $T_{RTV}/C_{RTV} \times 100\%$, wherein $T_{RTV}$: RTV of the treatment group; $C_{RTV}$: RTV of the negative control group. Therapeutic efficacy evaluation criteria: T/C %>60% was ineffective; T/C %≤60% with P<0.05 after being statistically processed was effective. The calculation formula of the tumor growth inhibition rate (TGI) was as follows:

$$TGI (\%) = \{[(CV_t - CV_0) - (TV_t - TV_0)]/(CV_t - CV_0)\} \times 100\%$$

$CV_t$ was the tumor volume at the end of administration in the control group, $CV_0$ was the tumor volume before administration to each cage in the control group, $TV_t$ was the tumor volume at the end of administration in the administration group, and $TV_0$ was the tumor volume before administration to each cage in the administration group. A t-test was performed for the difference in tumor volumes between the administration group and the control group. At the same time, the nude mice in each group were weighed twice a week to preliminarily evaluate the toxic side effects of the drugs. The pharmacodynamic results of each compound in this model were shown in Table 7 below.

CONCLUSIONS

Compared with 20 mpk of the known HSP90 inhibitor Ganetespib, the compound of formula (I) has a significantly superior antitumor effect in the BT-474 breast cancer cell transplanted mouse model at 10 mpk.

TABLE 7

In vivo pharmacodynamic test results of the compound of formula (I)

| | TGI (%) | | | | | |
|---|---|---|---|---|---|---|
| Test samples | day0 | day 7 | day 11 | day 18 (stop administration) | day 21 | day 35 |
| Vehicle | — | — | — | — | — | — |
| Ganetespib (20 mpk) | — | — | — | — | 124 | 108 |
| Compound of formula (I) (10 mpk) | — | — | — | — | 137 | 120 |
| Compound of formula (I) (20 mpk) | — | — | — | — | 135 | 129 |

What is claimed is:

1. A compound of formula (I) in crystalline form,

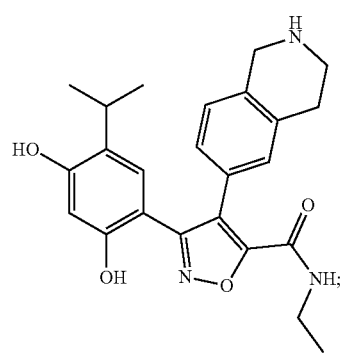

(I)

or a salt of the compound of formula (I), wherein the salt of the compound of formula (I) is selected from: trifluoroacetate, methanesulfonate, p-toluenesulfonate, citrate, maleate, fumarate, hydrobromide, phosphate or sulfate, or a compound of formula (II),

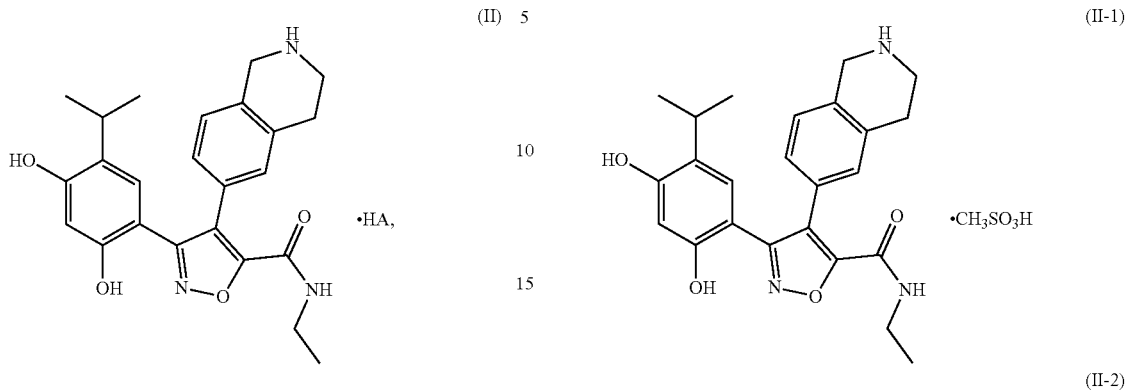

wherein HA is selected from trifluoroacetic acid, methanesulfonic acid, ρ-toluenesulfonic acid, citric add, maleic acid, fumaric acid, hydrochloric acid, hydrobromic acid, phosphoric acid, and sulfuric acid
wherein HA is selected from trifluoroacetic acid, methanesulfonic acid, ρ-toluenesulfonic acid, citric acid, maleic acid, fumaric acid, hydrochloric acid, hydrobromic acid, phosphoric acid, and sulfuric acid±characterized in that the X-ray powder diffraction pattern of the compound of formula (I) in crystalline form has diffraction peaks at the following 2θ angles: 10.66±0.2°, 15.09±0.2°, 19.17±0.2°.

2. The compound of formula (1) in crystalline form or the salt of the compound of formula (I) according to claim 1, characterized in that the X-ray powder diffraction pattern of the compound of formula (I) in crystalline form has diffraction peaks at the following 2θ angles: 10.66±0.2°, 11.41±0.2°, 15.09±0.2°, 19.17±0.2°, 20.43±0.2°, 22.19±0.2°, 25.76±0.2°.

3. The compound of formula. (1) in crystalline form or the salt of the compound of formula (I) according to claim 1, characterized in that a X-ray powder diffraction pattern of the compound of formula (I) in crystalline form has diffraction peaks at the following 2θ angles: 7.34±0.2°, 12.23±0.2°, 12.53±0.2°, 14.69±0.2°, 18.72±0.2°, 19.03±0.2°, 0.2°, 20.67±0.2°, 22.15±0.2°.

4. The compound of formula (I) in crystalline form or the salt of the compound of formula (I) according to claim 1, characterized in that a X-ray powder diffraction pattern of the compound of formula (I) in crystalline form has diffraction peaks at the following 2θ angles: 6.45±0.2°, 7.68±0.2°, 10.56±0.2°, 12.91±0.2°, 13.58±0.2°, 15.40±0.2°, 21.14±0.2°, 26.32±0.2°.

5. The compound of formula (I) in crystalline form or the salt of the compound of formula (I) according to claim 1, characterized in that a X-ray powder diffraction pattern of the compound of formula (I) in crystalline form has diffraction peaks at the following 2θ angles: 5.96±0.2°, 9.53±0.2°, 9.65±0.2°, 11.94±0.2°, 16.42±0.2°, 19.43±0.2°, 22.01±0.2°, 25.49±0.2°.

6. The compound of formula (I) in crystalline form or the salt of the compound of formula (I) according to claim 1, which is presented as a crystalline composition, wherein weight of the compound of formula (I) in crystalline form is 50% or more with respect to weight of the composition.

7. The compound of formula (I) in crystalline form or the salt of the compound of formula (I) according to claim 1, wherein the salt is selected from a compound represented by formula (II-1) or a compound represented by formula (II-2):

8. A pharmaceutical composition comprising the compound of formula (I) in crystalline form or the salt of the compound of formula (I) according to claim 1.

9. A method for treating a HSP90-mediated disease selected from cancer and neurodegenerative disorder, wherein the cancer includes: bladder cancer, breast cancer, colon cancer, kidney cancer, liver cancer, lung cancer including small cell lung cancer, esophageal cancer, gallbladder cancer, ovarian cancer, pancreatic cancer, gastric cancer, cervical cancer, thyroid cancer, prostate cancer, and skin cancer including squamous cell carcinoma; lymphatic hematopoietic tumors, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, and Burkitt's lymphoma; myeloid hematopoietic carcinomas, including acute and chronic myelogenous leukemia, myelodysplastic syndrome and promyelocytic leukemia; mesenchyme-derived cancer including fibrosarcoma and rhabdomyosarcoma; cancers of central and peripheral nervous system, including astrocytoma, neurocytoma, glioma, and neurilemmoma, melanoma, seminoma, teratocarcinoma, osteosarcoma, xeroderma pigmentosum, keratoxanthoma, thyroid follicular carcinoma, and Kaposi's sarcoma; and the neurodegenerative disorder includes: Alzheimer's disease, Parkinson's disease, Huntington's disease, multiple sclerosis, and spinal and bulbar muscular atrophy, comprising administering the compound of formula (I) in crystalline form or the salt of the compound of formula (I) according to claim 1 to a subject in need thereof.

10. The compound of formula (I) in crystalline form or the salt of the compound of formula (I) according to claim 2, characterized in that the X-ray powder diffraction pattern of the compound of formula (I) in crystalline form has diffraction peaks at the following 2θ angles: 10.66±0.2°, 11.41±0.2°, 15.09±0.2°, 17.85±0.2°, 19.17±0.2°, 19.60±0.2°, 20.43±0.2°, 21.81±0.2°, 22.19±0.2°, 25.76±0.2°.

11. The compound of formula (I) in crystalline form or the salt of the compound of formula (I) according to claim 10, characterized in that the X-ray powder diffraction pattern of the compound of formula (I) in crystalline form has diffraction peaks at the following 2θ angles: 10.66±0.2°, 11.41±0.2°, 15.09±0.2°, 15.84±0.2°, 17.85±0.2 °, 18.22±0.2°, 19.17 ±0.2°, 19.60±0.2°, 20.19±0.2°, 20.43±0.2°, 21.81±0.2°, 22.19±0.2°, 22.86±0.2°, 24.57±0.2°, 25.76±0.2°, 26.05±0.2°, 27.75±0.2°.

12. The compound of formula (I) in crystalline form or the salt of the compound of formula (I) according to claim 1, characterized in that a differential scanning calorimetry curve of the compound of formula (I) has a starting point of endothermic peaks at 198 ±5° C.

13. The compound of formula (I) in crystalline form or the salt of the compound of formula (I) according to claim 1, characterized in that a differential scanning calorimetry curve of the compound of formula (1) has a starting point of endothermic peaks at 55 ±5° C.

14. The compound of formula (I) in crystalline form or the salt of the compound of formula (I) according to claim 1, characterized in that a differential scanning calorimetry curve of the compound of formula (I) has a starting point of endothermic peaks at 108 ±5° C.

15. The compound of formula (I) in crystalline form or the salt of the compound of formula (I) according to claim 1, characterized in that a differential scanning calorimetry curve of the compound of formula W has a starting point of endothermic peaks at 141 ±5° C.

16. The compound of formula (I) in crystalline form or the salt of the compound of formula (I) according to claim 6, wherein weight of the compound of formula (I) in crystalline form is 70% or more with respect to weight of the composition.

17. The compound of formula (I) in crystalline form or the salt of the compound of formula (I) according to claim 16, wherein weight of the compound of formula (1) in crystalline form is 90% or more with respect to weight of the composition.

18. The compound of formula (I) in crystalline form or the salt of the compound of formula (I) according to claim 17, wherein weight of the compound of formula (I) in crystalline form is 95% or more with respect to weight of the composition.

* * * * *

UNITED STATES PATENT AND TRADEMARK OFFICE
CERTIFICATE OF CORRECTION

PATENT NO. : 10,851,071 B2
APPLICATION NO. : 16/318606
DATED : December 1, 2020
INVENTOR(S) : Xiaobing Yan et al.

It is certified that error appears in the above-identified patent and that said Letters Patent is hereby corrected as shown below:

In the Claims

At Column 33, Lines 20-23 (Claim 1, Lines 11-14), please delete "wherein HA is selected from trifluoroacetic acid, methanesulfonic acid, .rho.-toluenesulfonic acid, citric add, maleic acid, fumaric acid, hydrochloric acid, hydrobromic acid, phosphoric acid, and sulfuric acid".

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*